(12) United States Patent
Wu et al.

(10) Patent No.: US 11,282,132 B2
(45) Date of Patent: Mar. 22, 2022

(54) FRAMEWORKS AND METHODOLOGIES CONFIGURED TO ENABLE GENERATION AND UTILISATION OF THREE-DIMENSIONAL BODY SCAN DATA

(71) Applicant: mPort Ltd, Chatswood West (AU)

(72) Inventors: Tsung-Yuan Wu, Macquarie Park (AU); Dipra Ray, Macquarie Park (AU)

(73) Assignee: mPort Ltd, Chatswood West (AU)

( * ) Notice: Subject to any disclaimer, the term of this patent is extended or adjusted under 35 U.S.C. 154(b) by 387 days.

(21) Appl. No.: 15/528,840

(22) PCT Filed: Nov. 25, 2015

(86) PCT No.: PCT/AU2015/000719
§ 371 (c)(1),
(2) Date: May 23, 2017

(87) PCT Pub. No.: WO2016/081984
PCT Pub. Date: Jun. 2, 2016

(65) Prior Publication Data
US 2017/0345089 A1    Nov. 30, 2017

(30) Foreign Application Priority Data

Nov. 25, 2014   (AU) ................................ 2014904767
Apr. 29, 2015   (AU) ................................ 2015901507
(Continued)

(51) Int. Cl.
*G06Q 30/06*    (2012.01)
*G06T 19/00*    (2011.01)
(Continued)

(52) U.S. Cl.
CPC ......... *G06Q 30/0643* (2013.01); *G06F 3/048* (2013.01); *G06Q 30/02* (2013.01);
(Continued)

(58) Field of Classification Search
CPC ........... G06Q 30/0643; G06Q 30/0641; G06Q 30/0621; G06Q 30/0613; G06Q 30/0601;
(Continued)

(56) References Cited

U.S. PATENT DOCUMENTS 7,561,726 B2    7/2009   Lu et al.
8,764,651 B2    7/2014   Tran
(Continued)

FOREIGN PATENT DOCUMENTS

WO    2007089301 A2    8/2007
WO    2007096652 A2    8/2007
WO    2014183157 A1    11/2014

OTHER PUBLICATIONS

International Search Report, PCT/AU2015/000719, dated Apr. 6, 2016, 18 pages.

*Primary Examiner* — Kee M Tung
*Assistant Examiner* — Khoa Vu
(74) *Attorney, Agent, or Firm* — Nelson Mullins Riley & Scarborough LLP; Anthony A. Laurentano

(57) ABSTRACT

The present invention relates to frameworks and methodologies configured to enable generation and utilisation of three-dimensional body scan data. Various embodiments are described by reference to applications by which body scan data is collected, and/or subsequently utilised in the context of providing downstream functionalities, for example in the context of enabling users and/or business derive benefit from three-dimensional body scan data.

20 Claims, 30 Drawing Sheets

(30) Foreign Application Priority Data

| Apr. 29, 2015 | (AU) | 2015901508 |
|---|---|---|
| Apr. 29, 2015 | (AU) | 2015901509 |
| May 6, 2015 | (AU) | 2015901613 |
| May 6, 2015 | (AU) | 2015901615 |
| Jun. 15, 2015 | (AU) | 2015902265 |
| Jun. 15, 2015 | (AU) | 2015902267 |
| Jun. 17, 2015 | (AU) | 2015902315 |
| Jun. 19, 2015 | (AU) | 2015902369 |
| Jun. 19, 2015 | (AU) | 2015902371 |

(51) Int. Cl.

| *G06Q 30/02* | (2012.01) |
|---|---|
| *G16H 10/60* | (2018.01) |
| *G16H 30/20* | (2018.01) |
| *G06F 3/048* | (2013.01) |
| *G06Q 50/10* | (2012.01) |
| *G06T 17/00* | (2006.01) |

(52) U.S. Cl.
CPC ..... *G06Q 30/0601* (2013.01); *G06Q 30/0613* (2013.01); *G06Q 30/0621* (2013.01); *G06Q 30/0641* (2013.01); *G06Q 50/10* (2013.01); *G06T 19/00* (2013.01); *G16H 10/60* (2018.01); *G16H 30/20* (2018.01); *G06T 17/00* (2013.01)

(58) Field of Classification Search
CPC ........ G06Q 30/02; G06Q 50/10; G06F 3/048; G06T 19/00; G06T 17/00
See application file for complete search history.

(56) References Cited

U.S. PATENT DOCUMENTS

| 2007/0167837 | A1 | 7/2007 | Moyer et al. | |
|---|---|---|---|---|
| 2009/0099457 | A1* | 4/2009 | Barnes | A61B 5/107 600/476 |
| 2009/0254971 | A1* | 10/2009 | Herz | G06Q 30/0603 726/1 |
| 2010/0111370 | A1* | 5/2010 | Black | G06K 9/00369 382/111 |
| 2013/0110679 | A1* | 5/2013 | Spadafora | G06Q 30/0627 705/26.63 |
| 2013/0158968 | A1* | 6/2013 | Ash | G16H 40/63 703/11 |
| 2013/0187919 | A1* | 7/2013 | Medioni | G06T 17/00 345/420 |
| 2014/0222624 | A1* | 8/2014 | Custer | G06Q 30/0637 705/26.82 |
| 2014/0375635 | A1* | 12/2014 | Johnson | G06T 17/20 345/420 |
| 2016/0093085 | A1* | 3/2016 | Ray | A61B 5/1072 345/419 |
| 2020/0364533 | A1* | 11/2020 | Sareen | G06N 3/006 |

* cited by examiner

FRAMEWORKS AND METHODOLOGIES CONFIGURED TO ENABLE GENERATION AND UTILISATION OF THREE-DIMENSIONAL BODY SCAN DATA

CROSS REFERENCE TO RELATED APPLICATIONS

This application is a 35 U.S.C. 371 national stage filing of International Application No. PCT/AU2015/000719, filed on Nov. 25, 2015, Australian Application No. 2015902265, filed on Jun. 15, 2015; Australian Application No. 2015902267, filed on Jun. 15, 2015; Australian Application No. 2015901509, filed on Apr. 29, 2015; Australian Application No. 2015901508, filed on Apr. 29, 2015; Australian Application No. 2015902315, filed on Jun. 17, 2015; Australian Application No. 2015901507, filed on Apr. 29, 2015; Australian Application No. 2015902371, filed on Jun. 19, 2015; Australian Application No. 2015901615, filed on May 6, 2015; Australian Application No. 2015901613, filed on May 6, 2015; Australian Application No. 2015902369, filed on Jun. 19, 2015; and Australian Application No. 2014904767, filed on Nov. 25, 2014. The contents of the aforementioned applications are hereby incorporated by reference in their entireties.

FIELD OF THE INVENTION

The present invention relates to frameworks and methodologies configured to enable generation and utilisation of three-dimensional body scan data. Various embodiments are described by reference to applications by which body scan data is collected, and/or subsequently utilised in the context of providing downstream functionalities, for example in the context of enabling users and/or business derive benefit from three-dimensional body scan data.

BACKGROUND

Any discussion of the prior art throughout the specification should in no way be considered as an admission that such prior art is widely known or forms part of common general knowledge in the field.

There are a wide range of activities in business and human life where body dimensions are of significant importance. However, in general terms the extent to which the potential for using electronically defined data representative of body dimensions is quite limited.

SUMMARY OF THE INVENTION

One embodiment provides a computer implemented method for enabling purchase of customised gifts based on centralized management of data derived from three dimensional body scans, the method including:

authenticating a first user at a server device, the first user being associated with first user record data, wherein the first user data includes user sizing data;

providing an interface thereby to enable the first user to assign a gifting permission to one or more further users, each further user being associated with respective user record data;

receiving a request from a remote terminal, the request being indicative of:

a second user in a gift purchaser role; and the first user in a gift recipient role;

performing a determination process thereby to determine whether the second user has been assigned gifting permission by the first user, and in the case that the second user has been assigned gifting permission by the first user, releasing one or more aspects of data from the first user record data to the remote terminal, thereby to facilitate a transaction between a retailer and the second user in respect of a gift customised for the first user.

One embodiment provides a computer implemented method wherein the one or more aspects of data include delivery address information for the first user.

One embodiment provides a computer implemented method wherein the one or more aspects of data include data derived from the user sizing data.

One embodiment provides a computer implemented method wherein the data derived from the user sizing data includes a recommended size for a specified item.

One embodiment provides a computer implemented method wherein the data derived from the user sizing data enables graphical display of a relationship between an item's size and the first user's size.

One embodiment provides a computer implemented method wherein the first user is enabled to assign multiple levels of gifting permission to a specified further user.

One embodiment provides a computer implemented method wherein the multiple levels of gifting permission include:

(i) a first level which limits permissions such that a purchase is able to be delivered only to the first user; and (ii) a second level which provides additional permissions such that a purchase is able to be delivered other than to the first user.

One embodiment provides a computer implemented method wherein delivery to the first user includes either or both of: delivery to a delivery address associated with the first user's record data; and in-person pick-up by the first user.

One embodiment provides a computer implemented method wherein delivery to other than the first user includes either or both of: delivery to a delivery address associated with the second user's record data; and in-person pick-up by the second user.

One embodiment provides a computer implemented method wherein the sizing data is derived from a three dimensional body scan.

One embodiment provides a computer implemented method for enabling purchase of customised gifts based on centralized management of data derived from three dimensional body scans, the method including:

providing an interface that is configured to receive input indicative of a first user in a gift recipient role;

communicating with a remote server that maintains access to a repository of user data, thereby to cause authentication of the first user by reference to first user record data in the repository of user data, wherein the first user record data includes user sizing data; and receiving from the remote server data derived from the user sizing data, thereby to facilitate a transaction between a retailer and the second user in respect of a gift customised for the first user.

One embodiment provides a computer implemented method wherein the interface is additionally configured to receive input indicative of the second user, and wherein the method additionally includes communicating with the remote server thereby to cause authentication of the second user by reference to second user record data in the repository of user data.

One embodiment provides a computer implemented method including performing a determination process thereby to determine whether the second user has been assigned gifting permission by the first user, and in the case that the second user has been assigned gifting permission by the first user, releasing one or more aspects of data from the first user record data to the remote terminal, thereby to facilitate a transaction between a retailer and the second user in respect of a gift customised for the first user.

One embodiment provides a computer implemented method wherein the one or more aspects of data include delivery address information for the first user.

One embodiment provides a computer implemented method wherein the one or more aspects of data include data derived from the user sizing data.

One embodiment provides a computer implemented method wherein the data derived from the user sizing data includes a recommended size for a specified item.

One embodiment provides a computer implemented method wherein the data derived from the user sizing data enables graphical display of a relationship between an item's size and the first user's size.

One embodiment provides a computer implemented method wherein the first user is enabled to assign multiple levels of gifting permission to a specified further user.

One embodiment provides a computer implemented method wherein the multiple levels of gifting permission include:

(i) a first level which limits permissions such that a purchase is able to be delivered only to the first user; and (ii) a second level which provides additional permissions such that a purchase is able to be delivered other than to the first user.

One embodiment provides a computer implemented method wherein delivery to the first user includes either or both of: delivery to a delivery address associated with the first user's record data; and in-person pick-up by the first user.

One embodiment provides a computer implemented method wherein delivery to other than the first user includes either or both of: delivery to a delivery address associated with the second user's record data; and in-person pick-up by the second user.

One embodiment provides a computer implemented method wherein the sizing data is derived from a three dimensional body scan.

One embodiment provides a computer implemented method for enabling tracking of body shape variations, the method including:

authenticating a user $U_1$, the user $U_1$ being associated with first user record data, wherein the first user data includes a first set of user physical attribute data associated with a time n ($PAD_1T_n$), wherein the set of physical attribute data is derived from a three-dimensional body scanning process;

receiving input representative of further set of first user physical attribute data, the further set being associated with a time n+x ($PAD_1T_{n+x}$);

performing analysis of a relationship between $PAD_1T_n$ and $PAD_1T_{n+x}$; and providing output configured to enable rendering, at a client device associated with user $U_1$, a graphical object representative of the relationship between $PAD_1T_n$ and $PAD_1T_{n+x}$.

One embodiment provides a computer implemented method for enabling identification of users based on a combination of fitness objectives and physical body characteristics, the method including:

authenticating a user $U_1$ at a server device, the user $U_1$ being associated with first user record data, wherein the first user data includes user physical attribute data $PAD_1$, wherein the physical attribute data is derived from a three-dimensional body scanning process;

providing an interface configured to enable a user $U_1$ to define fitness objective data $FOD_1$;

associating the defined fitness objective data $FOD_1$ with the first user $U_1$ in an information system, wherein the information system maintains, for a plurality of users $U_1$ to $U_n$, and physical attribute data $PAD_1$ to $PAD_n$ and fitness objective data $FOD_1$ to $FOD_n$;

executing a comparison algorithm in respect of data maintained by the information system, wherein the comparison algorithm is configured to identify relationships between a given user $U_i$ and a given user $U_j$ based on a combination: (i) threshold similarity between $FOD_i$ and $FOD_j$; and (ii) threshold similarity between of $PAD_i$ and $PAD_j$.

One embodiment provides a computer implemented method for managing body scan information, the method including:

receiving, from a plurality of distributed scanning booth systems, body scan data respectively defined for a plurality of users;

maintaining user record data, wherein the user record data is configured to include, for each of a plurality of users, user registration data and user body scan data; and providing a user interface functionality, viewable via a third party platform, which enables filtering of garments for display to a given user based on the user's size as derived from the body scan data.

One embodiment provides a computer implemented method for displaying garment information to a user, the method including:

providing an interface that enables the user to view garment information;

identifying the user;

communicating with a remote server that maintains access to user record data, wherein the user record data is configured to include, for each of a plurality of users, user registration data and user body scan data; and filtering of garments for display to a given user based on the user's size as derived from the body scan data.

One embodiment provides a computer implemented method for providing product sizing information via a mobile device, the method including:

inputting, via the mobile device, data representative of a product;

transmitting, from the mobile device to a server, (i) data representative of the product; and (ii) data configured to enable authentication of a user of the mobile device;

receiving from the server data representative of user-specific product sizing information for the product; and rendering, via a user interface provided by the mobile device, the user-specific product sizing information for the product.

One embodiment provides a computer implemented method for providing product sizing information via a mobile device, the method including:

receiving, at a server device, from a remote mobile device: (i) data representative of a product; and (ii) data configured to enable authentication of a user of the mobile device;

processing the data configured to enable authentication of a user of the mobile device thereby to authenticate the user;

and following the authentication, accessing body sizing information associated with the user;

processing the data representative of the product based on (i) the body sizing information associated with the user; and (ii) set of sizing rules; thereby to determine user-specific product sizing information for the product; and transmitting to the mobile device data to enable rendering, via a user interface provided by the mobile device, the user-specific product sizing information for the product.

One embodiment provides a computer implemented method for managing body scan data, the method including:

maintaining access to a repository of body scan data, wherein the repository of body scan data includes a plurality of sets of body scan data derived from respective body scanning processes performed at distributed scanning booths;

maintaining access to a user record database, wherein the user record database includes user data records for a plurality of users, wherein each user data record is associated with one or more sets of body scan data; and providing a video game interface module, wherein the video game interface module is configured to perform a data exchange with a plurality of video game servers, wherein the data exchange includes:

delivery to a particular video game server of a set of body scan data associated with a user U1 in the user record database in response to authentication of user credentials associated with user U1 in the user record database, wherein the user credentials are transmitted via the video game server;

or delivery to a particular video game server of a set of body scan data associated with a user U1 in the user record database in response to authentication of user credentials associated with user U1 in a record database associated with the video game server, wherein the user credentials are transmitted via a scanning booth; or wherein the delivered set of body scan data is processed by the video game server thereby to enable generation of a virtual object based on the body scan data, wherein the virtual object is configured for rendering at a client device.

One embodiment provides a method wherein the data exchange includes delivery to a particular video game server of a set of body scan data associated with user U1 in the user record database in response to authentication of user credentials associated with a user U1 in the user record database, wherein the user credentials are transmitted via the video game server.

One embodiment provides a method wherein a user inputs the credentials associated with a user U1 via a user interface rendered at a client terminal that executes a video game associated with the video game server.

One embodiment provides a method wherein the data exchange includes delivery to a particular video game server of a set of body scan data associated with a user U1 in the user record database in response to authentication of user credentials associated with user U1 in a record database associated with the video game server, wherein the user credentials are transmitted via a scanning booth.

One embodiment provides a method wherein the scanning booth provides a user interface that enables a user to select a video game associated with the video game server, and input the of user credentials associated with a user U1 in a record database associated with the video game server.

One embodiment provides a computer implemented method for providing graphical data representative of forecasted body shape variations, the method including:

authenticating a user $U_1$, the user $U_1$ being associated with first user record data, wherein the first user data includes a first set of user physical attribute data associated with a time n ($PAD_1T_n$), wherein the set of physical attribute data is derived from a three-dimensional body scanning process;

processing the physical attribute data associated with time n ($PAD_1T_n$) based on the a selected forecasting protocol thereby to define forecasted user physical attribute data for user $U_1$ associated with a time n+x ($PAD_1T_{n+x}$);

providing output configured to enable rendering, at a client device associated with user $U_1$, a graphical object representative of $PAD_1T_{n+x}$.

One embodiment provides a computer implemented method for providing graphical data representative of forecasted body shape variations, the method including:

authenticating a user $U_1$, the user $U_1$ being associated with first user record data, wherein the first user data includes a first set of user physical attribute data associated with a time n ($PAD_1T_n$), wherein the set of physical attribute data is derived from a three-dimensional body scanning process;

processing the physical attribute data associated with time n ($PAD_1T_n$) based on the a selected forecasting protocol thereby to define forecasted user physical attribute data for user $U_1$ associated with a time n+x ($PAD_1T_{n+x}$);

providing output configured to enable rendering, at a client device associated with user $U_1$, a graphical object representative of $PAD_1T_{n+x}$.

One embodiment provides a hardware arrangement configured to provide body scan data to a body scan data management server, the arrangement including:

a plurality of discrete scanning units, wherein each scanning unit includes:

(i) a body that is configured to be mounted to a surface;

(ii) at least one camera device that is configured, upon mounting of the body to the surface, to capture scan data from within a scanning region;

a processing unit that is configured to process scan data derived from the plurality of discrete scanning units, thereby to define sets of body scan data;

a communications module that is configured to upload at least a subset of the sets of body scan data to the body scan data management server.

One embodiment provides a computer implemented method for managing body scan data, the method including:

receiving data representative of a selection of a customizable mechanical device;

identifying a size-based customisation protocol associated with the selected customizable mechanical device;

identifying a target user;

accessing body size data for the identified target user, wherein the body size data is obtained from a server that maintains access to body attribute data for a plurality of users, wherein the body attribute data is derived from 3D body scanning of each of the plurality of users;

applying the identified size-based customisation protocol to the accessed body size data, thereby to define equipment customisation data; and providing output data representative of the equipment customisation data.

One embodiment provides a computer implemented method for enabling user-user matching, the method including:

authenticating a user $U_1$ at a server device, the user $U_1$ being associated with first user record data, wherein the first user data includes user physical attribute data $PAD_1$, wherein the physical attribute data is derived from a three-dimensional body scanning process;

providing an interface configured to enable the first user to define data representative of desired physical attributes $DPA_1$;

associating the defined data representative of desired physical attributes $DPA_1$ with the first user $U_1$ in an information system, wherein the information system maintains, for a plurality of users $U_1$ to $U_n$, and physical attribute data $PAD_1$ to $PAD_n$ and desired physical attribute data $DPA_1$ to $DPA_n$;

executing a matching algorithm in respect of data maintained by the information system, wherein the matching algorithm is configured to identify a user-user match for a given user $U_i$ and a given user $U_j$ in the case that:

(i) the matching algorithm identifies $PAD_j$ as satisfying $DPA_i$; and/or (ii) the matching algorithm identifies $PAD_i$ as satisfying $DPA_j$; and providing output representative of the user-user match for users $U_i$ and $U_j$.

One embodiment provides a computer implemented method for enabling user-user matching, the method including:

providing an interface configured to enable a first user to define data representative of desired physical attributes;

accessing a database of physical attributes for a plurality of further users, the physical attributes being derived from three-dimensional body scanning;

providing output indicative of one or more of the further users for which their respective physical attributes satisfy the desired physical attributes, based on predefined satisfaction rules.

One embodiment provides a system configured for performing a method as described herein.

Reference throughout this specification to "one embodiment", "some embodiments" or "an embodiment" means that a particular feature, structure or characteristic described in connection with the embodiment is included in at least one embodiment of the present invention. Thus, appearances of the phrases "in one embodiment", "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

As used herein, the term "exemplary" is used in the sense of providing examples, as opposed to indicating quality. That is, an "exemplary embodiment" is an embodiment provided as an example, as opposed to necessarily being an embodiment of quality that would be categorised as "exemplary" as an indicator of quality.

It will be appreciated that any of the features of the methods and systems described herein can be provided independently or any combination with each other.

Furthermore, it will be appreciated that the methods and systems described herein can provide numerous advantages, including, but not limited to providing a system and method which can accurately measure a physical body and provide an accurate anatomically realistic representation of the physical body, typically in an image form. The image of the physical body and associated data generated (for example scanned information or measurement data) can be used to provide certain recommendations to the user of the physical body. In one example, these include fashion and/or health recommendations, although it will be appreciated that other applications of the system and method described herein also fall within the scope of this document.

BRIEF DESCRIPTION OF THE DRAWINGS

Embodiments of the technology are further described by way of example with reference to the accompanying drawings.

DETAILED DESCRIPTION

Figure 1A:
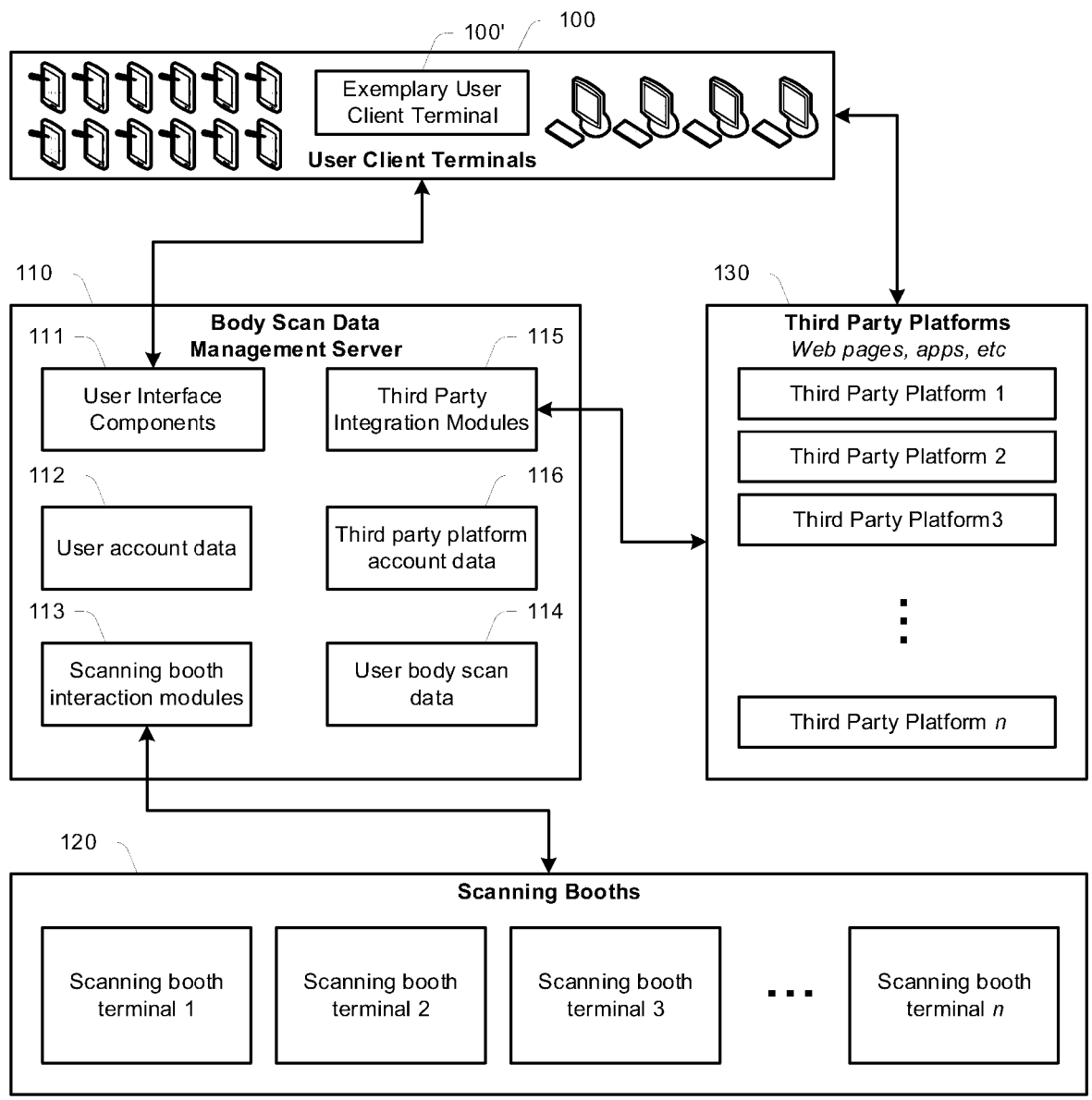
FIG. 1A to FIG. 1E illustrate frameworks according to various embodiments.

The present invention relates to frameworks and methodologies configured to enable generation and utilisation of three-dimensional body scan data. Various embodiments are described by reference to applications by which body scan data is collected, and/or subsequently utilised in the context of providing downstream functionalities, for example in the context of enabling users and/or business derive benefit from three-dimensional body scan data.

The technology herein described relates, in some embodiments, to frameworks and methodologies for enabling purchase of customised gifts based on centralized management of data derived from three dimensional body scans. Embodiments have been developed particularly for enabling a purchaser enter into a transaction with a retailer (for example online or in-store) thereby to procure a gift for a recipient. In the case that predefined conditions are met, a server device communicates to the retailer sizing information relevant to the purchase based on stored data relating to the recipient. Although embodiments described herein are focussed on implementations whereby that sizing information is derived from three dimensional body scans, in other embodiments the sizing information is derived via other processes.

The technology herein described relates, in some embodiments, to frameworks and methodologies for enabling purchase of customised gifts based on centralized management of data derived from three dimensional body scans. Embodiments have been developed particularly for enabling a purchaser enter into a transaction with a retailer (for example online or in-store) thereby to procure a gift for a recipient. In the case that predefined conditions are met, a server device communicates to the retailer sizing information relevant to the purchase based on stored data relating to the recipient. Although embodiments described herein are focussed on implementations whereby that sizing information is derived from three dimensional body scans, in other embodiments the sizing information is derived via other processes.

The technology herein described relates, in some embodiments, to frameworks and methodologies for enabling purchase of customised gifts based on centralized management of data derived from three dimensional body scans. Embodiments have been developed particularly for enabling a purchaser enter into a transaction with a retailer (for example online or in-store) thereby to procure a gift for a recipient. In the case that predefined conditions are met, a server device communicates to the retailer sizing information relevant to the purchase based on stored data relating to the recipient. Although embodiments described herein are focussed on implementations whereby that sizing information is derived from three dimensional body scans, in other embodiments the sizing information is derived via other processes.

The technology herein described relates, in some embodiments, to technology including filtering of web results and/or filtering display of inventory items in online garment viewing and/or purchase platforms via centralized management of data derived from three dimensional body scans.

The technology herein described relates, in some embodiments, to frameworks and methodologies for enabling purchase of customised gifts based on centralized management of data derived from three dimensional body scans. Embodiments have been developed particularly for enabling a purchaser to enter into a transaction with a retailer (for example online or in-store) thereby to procure a gift for a recipient. In the case that predefined conditions are met, a server device communicates to the retailer sizing information relevant to the purchase based on stored data relating to the recipient. Although embodiments described herein are focussed on implementations whereby that sizing information is derived from three dimensional body scans, in other embodiments the sizing information is derived via other processes.

The technology herein described relates, in some embodiments, to 3D body scan management, and in some embodiments to frameworks and methodologies configured to enable interaction between scanning booth networks and video game servers. Embodiments have been developed particularly to provide an intuitive framework that enables users to obtain personalised virtual bodies for use in video games. However, the technology is applicable to a wider range of implementation environments.

The technology herein described relates, in some embodiments, to frameworks and methodologies for enabling purchase of customised gifts based on centralized management of data derived from three dimensional body scans. Embodiments have been developed particularly for enabling a purchaser to enter into a transaction with a retailer (for example online or in-store) thereby to procure a gift for a recipient. In the case that predefined conditions are met, a server device communicates to the retailer sizing information relevant to the purchase based on stored data relating to the recipient. Although embodiments described herein are focussed on implementations whereby that sizing information is derived from three dimensional body scans, in other embodiments the sizing information is derived via other processes.

The technology herein described relates, in some embodiments, to frameworks and methodologies for enabling purchase of customised gifts based on centralized management of data derived from three dimensional body scans. Embodiments have been developed particularly for enabling a purchaser enter into a transaction with a retailer (for example online or in-store) thereby to procure a gift for a recipient. In the case that predefined conditions are met, a server device communicates to the retailer sizing information relevant to the purchase based on stored data relating to the recipient. Although embodiments described herein are focussed on implementations whereby that sizing information is derived from three dimensional body scans, in other embodiments the sizing information is derived via other processes.

The technology herein described relates, in some embodiments, to frameworks and methodologies for enabling purchase of customised gifts based on centralized management of data derived from three dimensional body scans. Embodiments have been developed particularly for enabling a purchaser enter into a transaction with a retailer (for example online or in-store) thereby to procure a gift for a recipient. In the case that predefined conditions are met, a server device communicates to the retailer sizing information relevant to the purchase based on stored data relating to the recipient. Although embodiments described herein are focussed on implementations whereby that sizing information is derived from three dimensional body scans, in other embodiments the sizing information is derived via other processes.

The technology herein described relates, in some embodiments, to frameworks and methodologies for enabling purchase of customised gifts based on centralized management of data derived from three dimensional body scans. Embodiments have been developed particularly for enabling a purchaser enter into a transaction with a retailer (for example online or in-store) thereby to procure a gift for a recipient. In the case that predefined conditions are met, a server device communicates to the retailer sizing information relevant to the purchase based on stored data relating to the recipient. Although embodiments described herein are focussed on implementations whereby that sizing information is derived from three dimensional body scans, in other embodiments the sizing information is derived via other processes.

General Overview

The technology herein described is in some cases implemented in the context of a framework that provides for distributed collection and utilisation of body scan data, primarily body size and shape information. This data is preferably collected via distributed hardware devices, which may include autonomous scanning booths and/or other scanning hardware (including from image-based, stereoscopic, microwave, infrared, and other scanning technologies).

In some embodiments a scanning booth includes user interface components which implement a predefined logical process thereby to guide a user though a scanning procedure.

Body scan data is then uploaded to a central server, and via this server is made available to one or more third party platforms, such as websites and software applications (for example using APIs, widgets, and the like). This enables the third party platforms to implement functionalities which leverage body scan data. Examples of such functionalities include selection of appropriately sized clothing, monitoring of health and fitness, rating/ranking, competitions, and so on.

FIG. 1A illustrates an overall framework according to one embodiment. Exemplary implementations of various components within this framework are described in more detail further below.

FIG. 1A centres around a body scan data management server 110. This server may, in practical embodiments, be defined by one or more individual computing devices, optionally distributed over a number of physical locations. Server 110 is configured to communicate with:

- User client terminal 100, which may include the likes of personal computers, notebooks, smartphones, tablets, gaming consoles, and the like. For example, these client terminals execute respective web browser applications, which enable local rendering of user interface components provided by a user interface component module 111 of server 110. These user interface components provide users with access to functionalities native to server 110, which preferably includes account management (for example registration of a new account, and modification of existing account details, with user account data being maintained in a repository 112) and in some cases scan management (for example modification of avatars, deletion of scan data, and so on).
- Scanning booths 120, which may include user-driven autonomous booths (such as those described below) and in some embodiments other scanning booths. Scanning booth interaction modules 113 are responsible for enabling interaction between scanning booths 120 and server 110. This may include user account data management (for example where a user is enabled to register and/or login via a user interface provided at a scanning booth terminal), terminal maintenance (for example monitoring, downloading of software patches/updates), serving of advertising and/or promotional content, and so on.
- Third party platforms 130, which may include the likes of websites, proprietary software applications (including, but not limited to, mobile apps). Third party integration modules 115 allow server 110 to communicate with each of platforms 130, preferably via a plurality of technological approaches. This may include widget based approaches (where code served by server 110 is embedded within a web page provided by one of platforms 130 and rendered at a given one of client terminals 100, API-based approaches (whereby a third party platform communicates with and interacts with server 110 via a predefined communications protocol), and other approaches.

Third party platform account data 116 include data specific to each third party platform, thereby to allow either or both of (i) monetisation of services provided to those platforms on a monitored (for example per-use) basis; and (ii) maintaining platform-specific information (such as garment sizing data) thereby to allow tailored customisation of data and/or functionality provided via modules 115.

Various examples of widgets and other functionalities provided by server 110 to platforms 130 are discussed in additional detail further below.

Autonomous User-Driven Scanning Overview

Embodiments described herein are primarily focussed on arrangements whereby scanning booths provide autonomous user-driven scanning. This means that a scanning booth provides user interface and user stimuli components which implement a logical process thereby to guide a user through a body-scanning procedure without intervention by a second human user. That is, a user is enabled to approach a booth, and have a user interface guide them through an entire scanning process, from login (or registration in the context of a non-registered user) through to scan completion (and in some embodiments avatar approval).

In general terms, a scanning booth configured to provide an autonomous user-driven scanning includes the following components:

- A user interface which provides a user interface thereby to enable a user to identify with the booth. This may include either or both of local registration (i.e. provision of personal information and the like thereby to create a new user account) and user login. A user login may include providing user credentials, such as a username and password, defined subject to a previous local registration or a previous remote registration (using a terminal 100 in communication with server 110). Various technological means for user identification may be used, including the likes of NFC devices, biometrics, electronic device recognition, and so on.
- A user interface and associated stimuli devices (for example visual and/or audible stimuli devices) configured to enable delivery of user instructions, thereby to enable a scan. These instructions include (i) preparation (for example clothing removal), (ii) stance and posture (for example positioning relative to defined feet positions and body position, preferably assisted by way of visual stimuli and automated feedback), and other such instructions. This allows automated scanning hardware (preferably in the form of infrared sensors) to collect body scan data from a body that is in a predefined desired stance and position. It will be appreciated that this greatly assists in analysis of collected measurements.
- Scanning components, such as infrared sensors, which are configured to determine body scan measurements. These measurements are used thereby facilitate downstream functionalities, for example avatar generation.
- A user interface which guides a user through avatar generation and approval. Following approval, body scan data is transmitted to server 110 thereby to be available for downstream use.

The user interfaces described above may be delivered by one or more screens, driven by one or more computing terminals.

FIG. 1A relates to an arrangement whereby users visit scanning booths 120 thereby to have respective sets of body scan data defined and made available via server 110. For example, such scanning booths are preferably provided in public locations, such as shopping malls and the like.

Figure 1B:
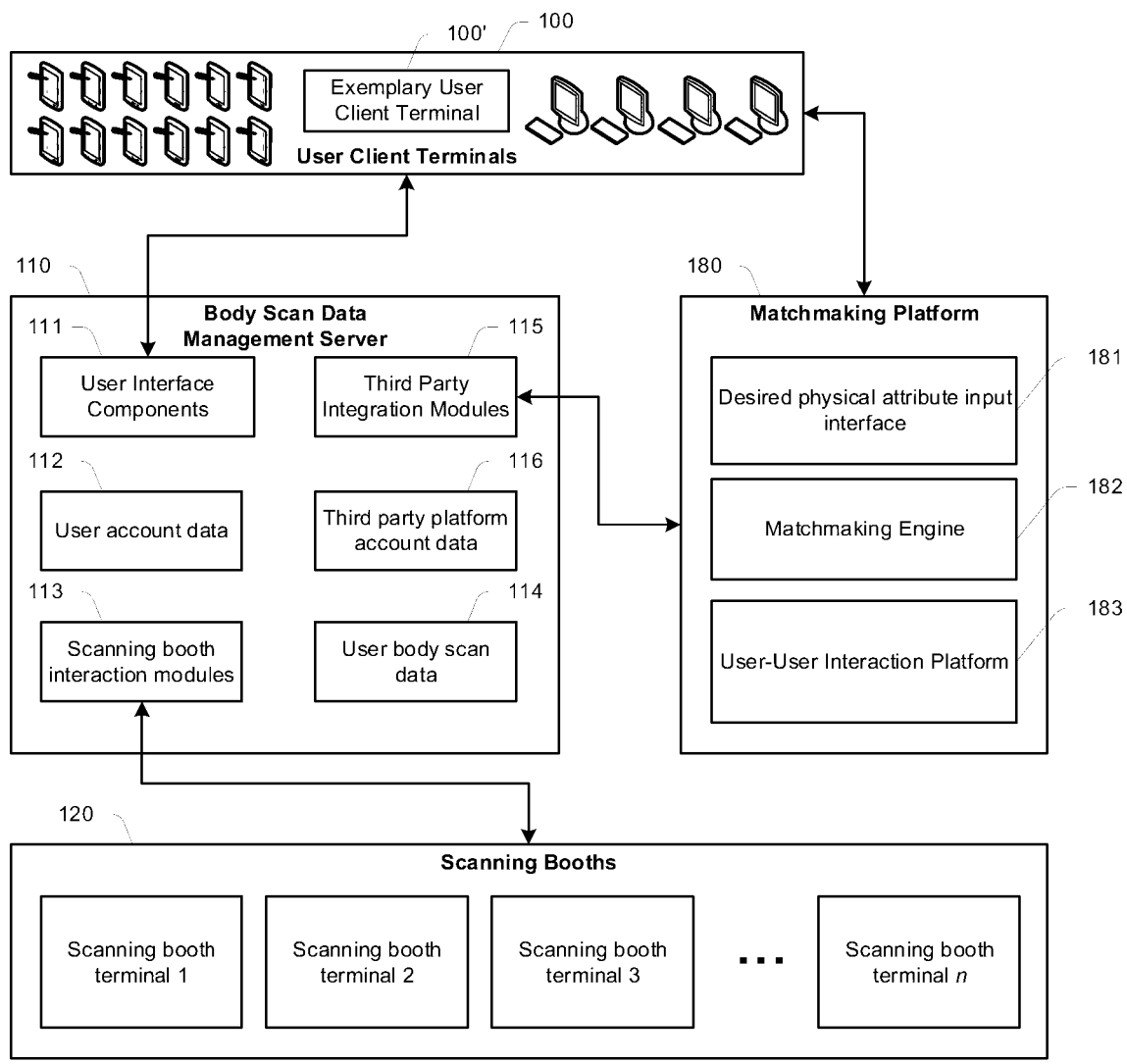
Figure 1C:
Figure 1D:
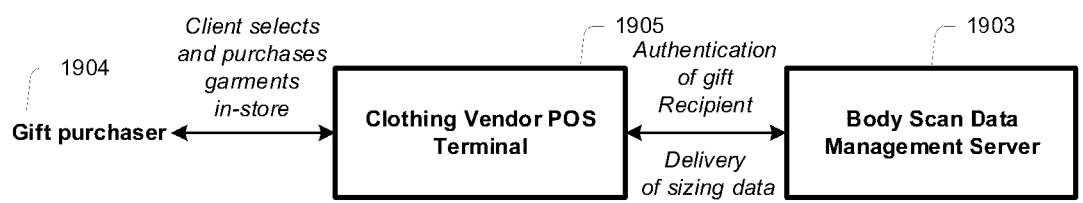
Figure 1E:
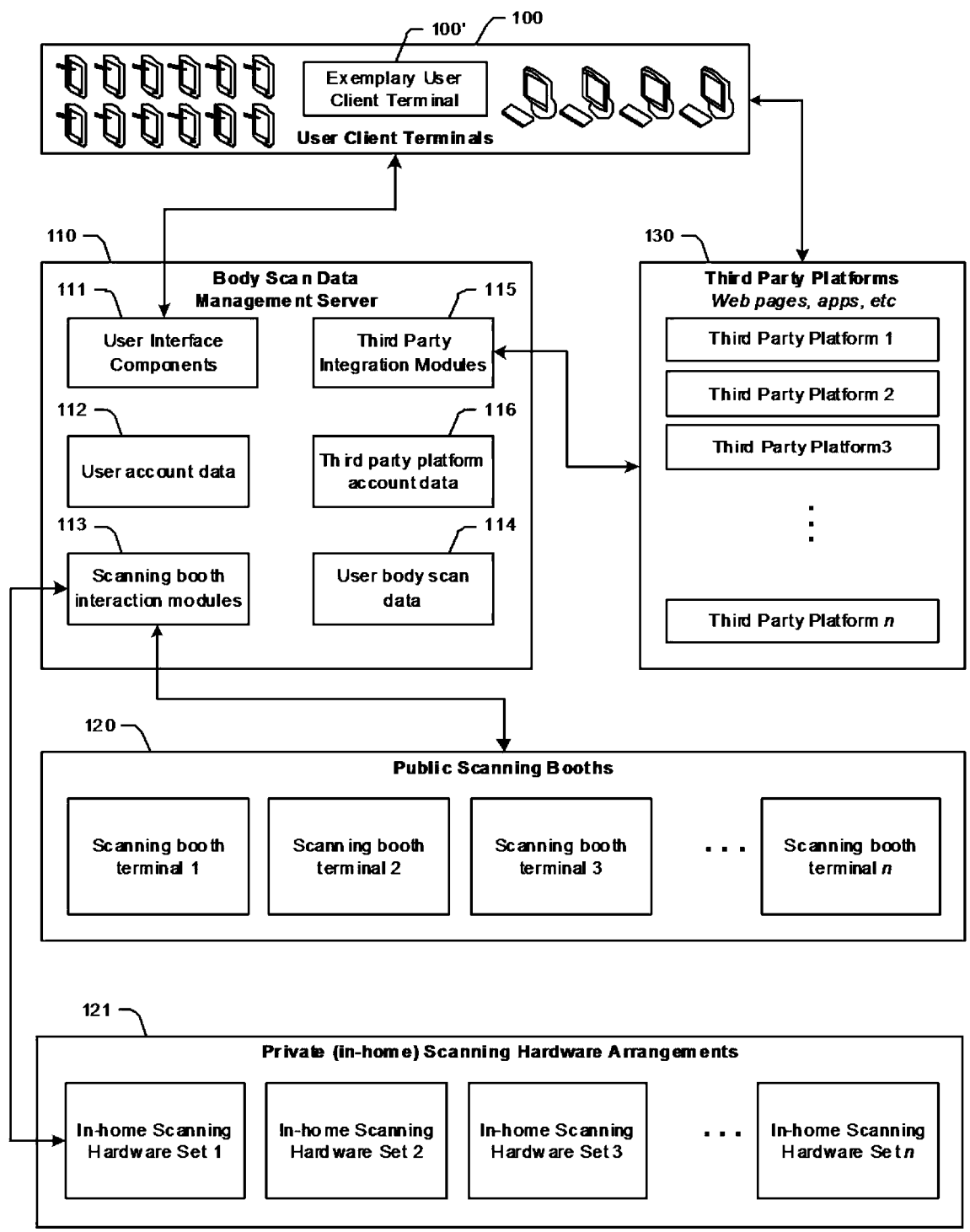

In some embodiments, such as FIG. 1E, server 110 is configured to additionally interact with private (in-home) scanning hardware arrangements 121. In general terms, arrangements 121 are defined by one or more hardware devices which are able to be installed in home environments, thereby to allow the defining of body scan data in such an environment. In practice, a driving factor is to enable users to undergo body scanning in an environment where they are already accustomed/comfortable being naked. For example, the scanning hardware arrangements are configured to be installed in locations such as bathrooms and bedrooms. This not only assists in providing an enhanced user experience through comfort, but also through efficiency (given that body scan data is able to be obtained far more conveniently, potentially even on daily basis).

In general terms, any functionality provided via server 110 is equally able to be provided to users of arrangements 121 and arrangements 120.

Figure 6A:
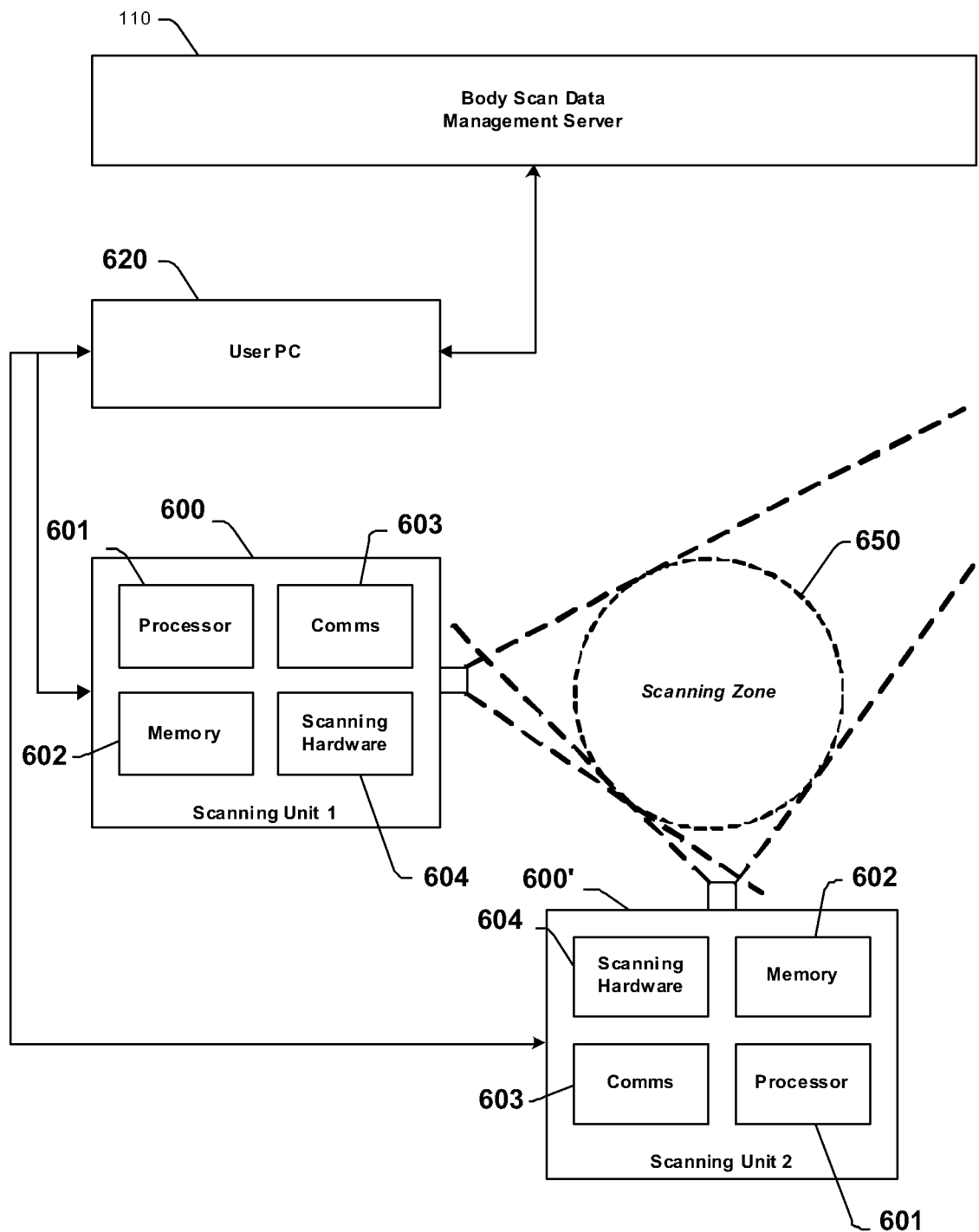
FIG. 6A to FIG. 6C illustrate exemplary scanning arrangements.
Figure 6B:
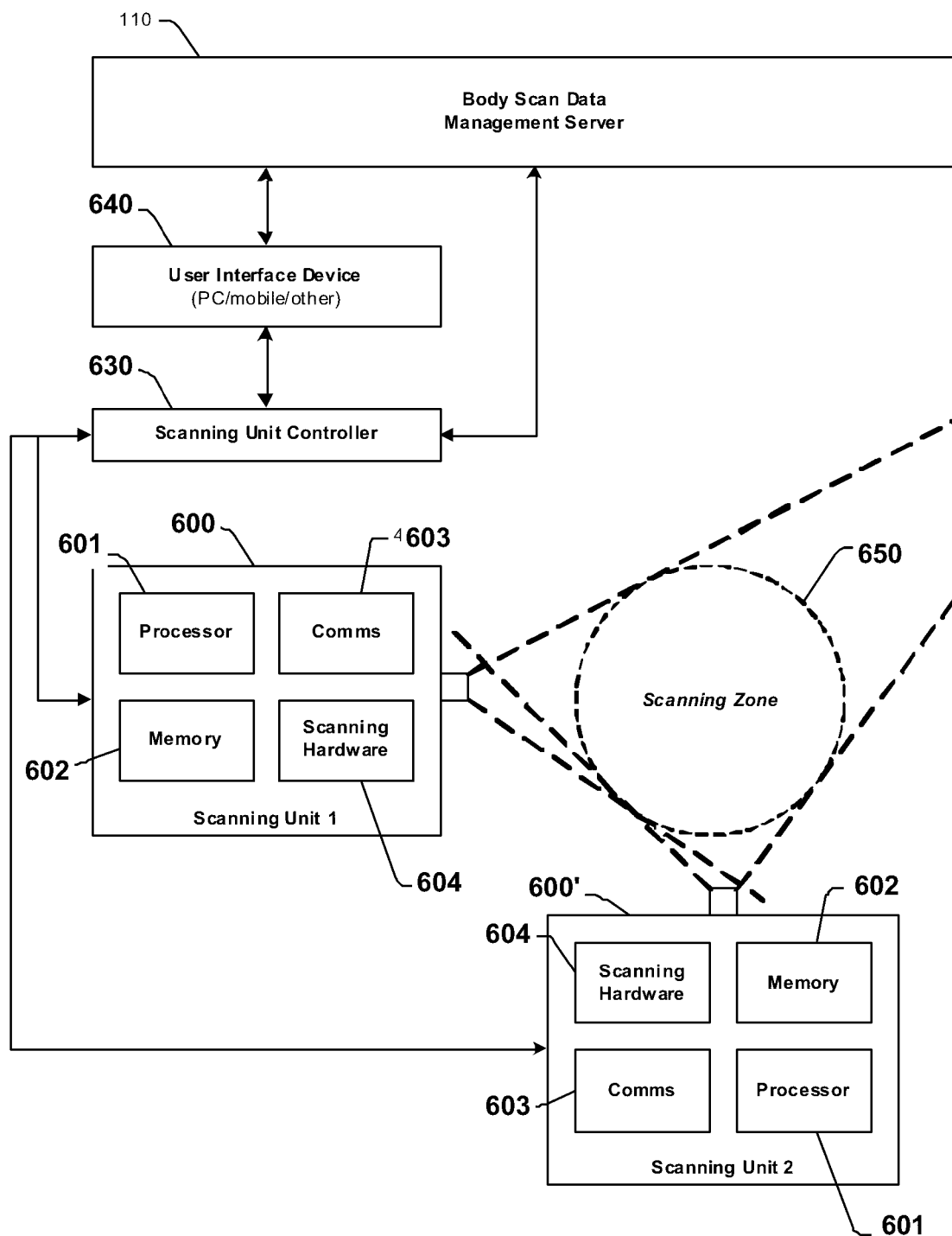
Figure 6C:
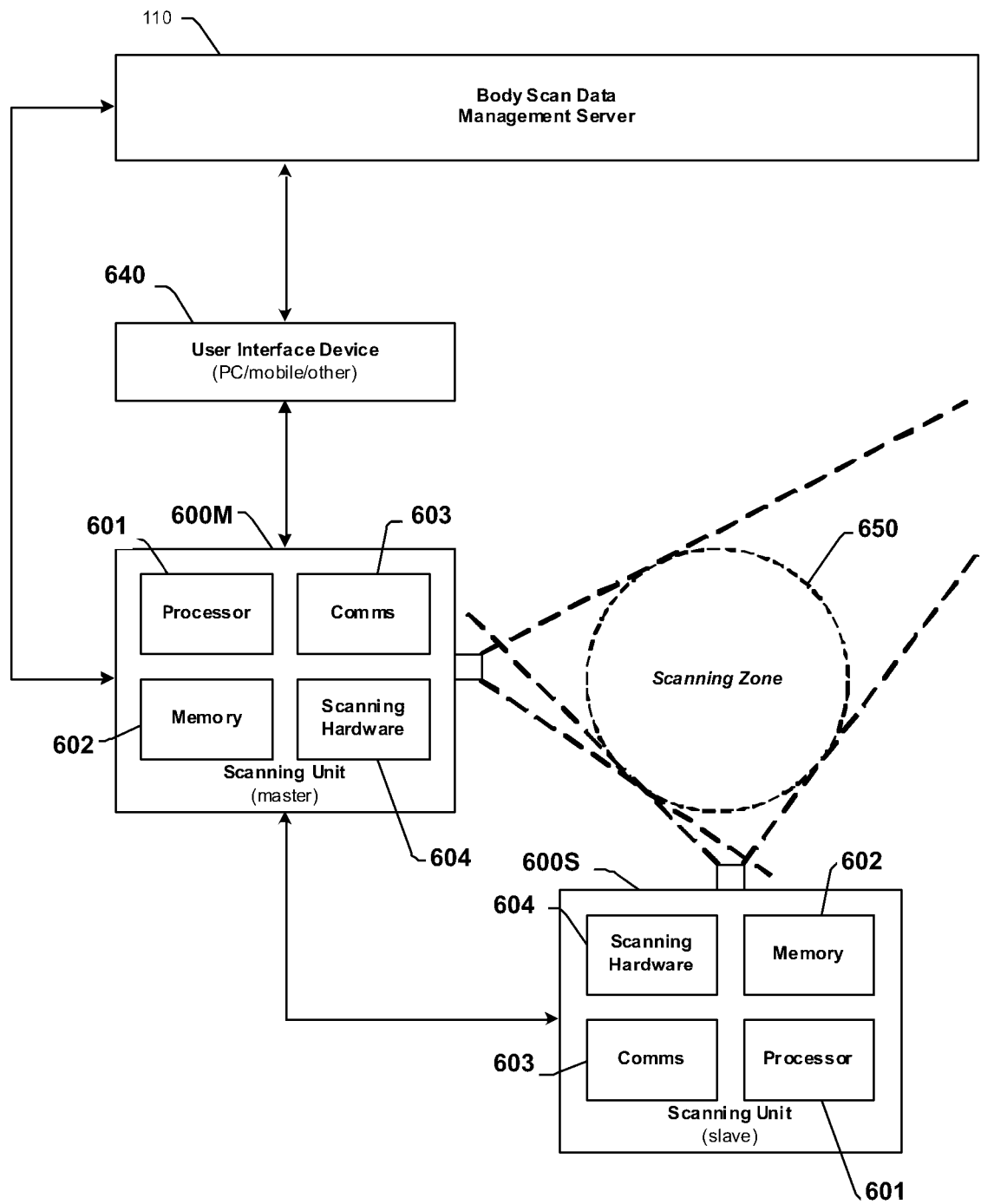

FIG. 6A to FIG. 6C illustrate exemplary in-home scanning hardware arrangements. In overview, each exemplary arrangement includes a plurality of discrete scanning units. Each scanning unit includes:

(i) A body that is configured to be mounted to a surface. For example, in some embodiments this includes a wall mounting formation. Other exemplary mounts include clamps and the like that are configured to be coupled to doors and/or door frames, and mounts that attach to stands (for example tripod type stands).

(ii) At least one camera device that is configured, upon mounting of the body to the surface, to capture scan data from within a scanning region. For example, camera devices such as infrared scanning cameras, depth sensing cameras, and the like, may be used. In some embodiments the camera device is adjustably mounted (for example on a pivot) thereby to enable adjustment of a location of the scanning region. In practice, the respective camera devices of the multiple scanning units are directed to define a common overlapped scanning one in which a user is contained for the purpose of body scanning.

A processing unit is configured to process scan data derived from the plurality of discrete scanning units, thereby to define sets of body scan data. In a preferred embodiment the processing unit obtains scan data from multiple angles (using the multiple discrete scanning units) and uses this to compile data into a single combined scan model. This in some embodiments includes point cloud data. In some embodiments defining a given set of body scan data includes processing a plurality of time-synchronised sets of scan data from the discrete scanning units. In some embodiments a given set of body scan data includes identifying one or more known body poses (for example by applying a video analysis algorithm thereby to determine a time when a known body pose is adopted, and utilise body scan data for that time).

The processing unit is in some cases provided by one of the scanning units, and in some cases by an alternate device (examples are described below).

A communications module is configured to upload at least a subset of the sets of body scan data to the body scan data management server. The communications module is in some cases provided by one of the scanning units, and in some cases by an alternate device (examples are described below).

In some embodiments, the scanning process utilises algorithms that are configured to defined three-dimensional body scan data based on scanning of a moving human body. For example, an overall set of data requirements is predefined, this representing body parts, and scan data (for example point cloud data) is collected during body movements until the predefined data requirements are satisfied. This accounts for situations where the scanning zone defined discrete camera units has "blind spots", which necessitate movement before a full human body is captured.

Some embodiments implement "passive scanning", whereby a user is autonomously scanned without providing a positive scanning request, for example based on a motion sensing trigger provided by one or more of the scanning units. Scan data is only defined in the case that adequate capture occurs during an instance of passive scanning to meet the predefined data requirements. In some cases additional data requirements are implemented, for example a data requirement that discounts data obtained in the event that a user is detected to be wearing clothing.

In some embodiments an active scanning approach is used, whereby a user provides a command to scan (which is optionally either by interaction with a user interface device, a button on a scanning unit, or by adopting a specific pose in the scanning zone). In some such embodiments a user adopts and holds one or more predefined poses thereby to assist an effective body scan.

In the example of FIG. 6A, two scanning units 600 and 600' are mounted thereby to define a scanning zone 650. Units 600 and 600' each include a microprocessor 601 coupled to a memory module 602 and a communications module (for example WiFi or another wireless communications protocol) 603. These components configure scanning hardware 604 to capture data, in the form of 3D scan data, for objects contained in scanning zone 650. Units 600 and 600' provide scanning data to a user PC 620, which executes a software application that is configured to process the scan data thereby to define body scan data for upload to server 110.

In the example of FIG. 6B, PC 620 is replaced by a scanning unit controller 630, which provides processing and upload capabilities, and a user interface device 640, which may be a smartphone or the like. A user operates the user interface device thereby to perform configuration operations for controller 630 and scanning units 600 and 600'. For example, these include operations relevant to scanning unit discovery, scanning hardware calibration/configuration, and so on. The user interface device is also configured to interact with server 110. For example, a proprietary app executes on device 640 which enables both interaction with the scanning units and access to functionalities provided by server 110.

In the example of FIG. 6C, functionalities of scanning unit controller 630 are taken on by one of the scanning units, which operates as a master scanning unit 600M. The other scanning unit operates as a slave scanning unit 600S. In some embodiments master and slave devices are different from a hardware perspective. For example: greater processing power may be provided at the master; slave-master communications may be via a first communications technology (such as Bluetooth) whereas the master has WiFi for upload functionaries; the master may include additional user interface components; and so on. In other embodiments all scanning units include the same hardware, and one is configured to adopt a master role.

In some embodiments component (such as the processing component) is configured to identify a user, such that a given set of body scan data is associated with the identified user. For example, that component is configured to identify a user is configured to compare a new set of body scan data with a plurality of sets of pre-existing body scan data that are associated with respective known users, thereby to determine whether the new set of body scan data represents one of the known users. Or, more generally, known users are autonomously identified based on visual or other characteristics able to be identified in body scan data (even in spite of minor body attribute variations).

In some embodiments at least one of the discrete scanning units is configured to perform a monitoring process, and initiate a body scanning process in response to an output of the monitoring process. For example, this may be a motion tracking process, or a process that identifies prescribed motions (for example a user adopting a specific body pose). This enables automated triggering of a body scanning process. However, in some embodiments a body scanning process is initiated in response to user input.

Gift Management Functionalities

As noted, the technology herein described relates to frameworks and methodologies for enabling purchase of customised gifts based on centralized management of data derived from three dimensional body scans. Embodiments have been developed particularly for enabling a purchaser enter into a transaction with a retailer (for example online or in-store) thereby to procure a gift for a recipient. In the case that predefined conditions are met, a server device communicates to the retailer sizing information relevant to the purchase based on stored data relating to the recipient. Although embodiments described herein are focussed on implementations whereby that sizing information is derived from three dimensional body scans, in other embodiments the sizing information is derived via other processes.

In the embodiments described below, a gift may be any "item". Examples include clothing, jewelry, and the like, which are typically sized by reference to the size of an intended user. However, the technology is not limited by reference to such examples. There exist a wider range of items which might be sized relative to attributes of an intended user, including size attributes relating to any one or more of dimensions, shape, height, weight, and so on. Other examples of items particularly suitable in the context of this technology include (but are not limited to) sporting equipment, furniture, fashion accessories, vehicles, and fashion accessories.

In overview, gift customization functionalities enable a gift purchaser to purchase an item for a gift recipient, and have the item size determined by reference to sizing data stored in relation to the gift recipient. Embodiments find application in each of:

Online stores, in which case elements in a web page are configured to provide a gift purchaser with access to gifting functionalities described herein. For example, a gift purchaser interacts with an object to identify that a proposed online purchase is a gift, and a gift sizing interface is provided thereby to replace a manual size selection control. An example is shown in FIG. 1C, in which a client terminal 1901 interacts with a clothing vendor web portal 1902, that portal in turn communicating with a body scan management server 1903 (which my in some embodiments correspond directly to server 1).

Physical stores, in which case an interface is provided on a terminal (such as a POS terminal), which is preferably controlled by a store assistant thereby to enable the store assistant to assist a gift purchaser with a transaction. An example is shown in FIG. 1D, in which a human gift purchaser 1904, via a shop assistant, interacts with a vendor POS terminal 1905, which in turn communicates with body scan management server 1903.

A server device (such as server 110) is configured to interact with either an online store platform or in-store terminal thereby to identify a gift recipient user, and provide data derived from the gift recipient user's sizing data thereby to facilitate completion of a gift transaction, wherein the gift item is sized customised for the recipient.

One embodiment provides a computer implemented method for enabling purchase of customised gifts based on centralized management of data derived from three dimensional body scans. This method is performed at a server such as server 110. The method includes authenticating a first user at a server device, the first user being associated with first user record data, wherein the first user data includes user sizing data. For example, the user logs on via a website. An interface is provided thereby to enable the first user to assign a gifting permission to one or more further users, each further user being associated with respective user record data. Permissions may be assigned on a global basis, on a user-category basis, or on a per-user basis. In some cases there are multiple assignable permission levels (as discussed further below).

At a subsequent point in time, the server is configured to receive a request from a remote terminal, the request being indicative of: a user in a gift purchaser role; and a user in a gift recipient role. The server then performs a determination process thereby to determine whether the gift purchaser user has been assigned gifting permission by the gift recipient user, and in the case that the gift purchaser user has been assigned gifting permission by the gift recipient user, one or more aspects of data are transmitted from (or derived from) the gift recipient's user record data to the remote terminal, thereby to facilitate a transaction between a retailer and the gift purchaser user in respect of a gift, the gift being hence customised for the gift recipient user. The one or more aspects of data may include delivery address information for the gift recipient user. More importantly, the one or more aspects of data include data derived from the user sizing data.

The above paragraph assumes that both the purchaser and recipient are registered with the server. However, in some embodiments only the recipient need be registered (hence allowing unregistered users to purchase gifts for registered users). However, it should be appreciated that there are various significant advantages associated with an arrangement whereby both purchaser and recipient are authenticated by reference to a common system, whether directly or indirectly (for example via $3^{rd}$ party systems).

The data derived from sizing data may take various forms. These include (but are not limited to) the following examples:

Providing user size data, thereby to enable a store-side determination of an appropriate item size.

Providing an item size recommendation, based on a server-side determination of an appropriate item size, requiring server-side knowledge of the item's sizes.

Providing data thereby to enable a graphical display of a relationship between an item's size and the first user's size. For example, this may provide a representation of item fit relative to a three dimensional avatar defined based on the user's measurements (which may allow subjective size selection based on visual analysis of multiple sizes on the avatar).

The transaction is then able to be completed with size selection based on known defined sizing for the recipient. In some embodiments the purchase is enabled to select a size other than that which is recommended by the system.

In some embodiments a user is enabled to assign multiple levels of gifting permissions to specified further users. The multiple levels of gifting permission include, in a preferred embodiment:

(i) a first level which limits permissions such that a purchase is able to be delivered only to the first user; and (ii) a second level which provides additional permissions such that a purchase is able to be delivered other than to the first user (for example delivery to a delivery address associated with the second user's record data, a delivery address nominated by the second user, in-person pick-up by the second user, and so on).

In relation to (i), delivery to the first user may include either or both of: delivery to a delivery address associated with the first user's record data; and in-person pick-up by the first user. This is intended to keep the gift recipient's sizing information private from the purchaser (as the purchaser will not know what item size was ultimately purchased). Such privacy is not maintained in relation to (ii), as the purchaser will have possession of the item and would typically be able to identify the size.

Another embodiment provides a computer implemented method for enabling purchase of customised gifts based on centralized management of data derived from three dimensional body scans, being a method performed at an in-store terminal (such as terminal 1905) or a web store portal (such as portal 1902). The method includes providing an interface that is configured to receive input indicative of a first user in a gift recipient role. For example, an email address is preferably used. The method then includes communicating with a remote server that maintains access to a repository of user data (such as server 1903), thereby to cause authentication of the gift recipient user by reference to user record data in a repository of user data. Then, data is received from the server, including data derived from the recipient user's sizing data, thereby to facilitate a transaction between a retailer and the second user in respect of a gift customised for the first user.

In some cases the method additionally includes communicating with the remote server thereby to cause authentication of the gift purchaser user by reference to user record data in the repository of user data. The method may additionally include, in the case that users adding gifting permissions, performing a determination process thereby to determine whether the purchaser user has been assigned gifting permission by the recipient user, and in the case that the purchaser user has been assigned gifting permission by the recipient user, releasing one or more aspects of data from the recipient user record data.

Figure 2A:
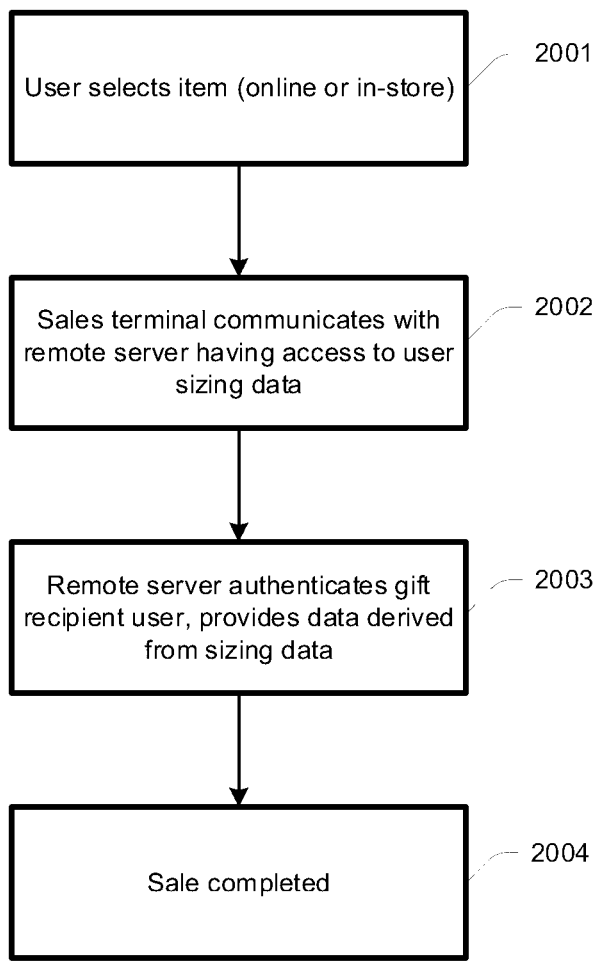
FIG. 2A to FIG. 2N illustrate methods according to various embodiments.

FIG. 2A illustrates a method showing an overall gifting process flow. A user selects an item (online or in-store) at 2001. A sales terminal (in store, or a "sales terminal" in the context of an online store platform) then communicates with a remote server that maintains user sizing data at 2002, and the server provides sizing data subject to authentication at 2003. The sale is completed at 2004. In some embodiments sizing information is provided following completion of a sale.

Figure 2B:
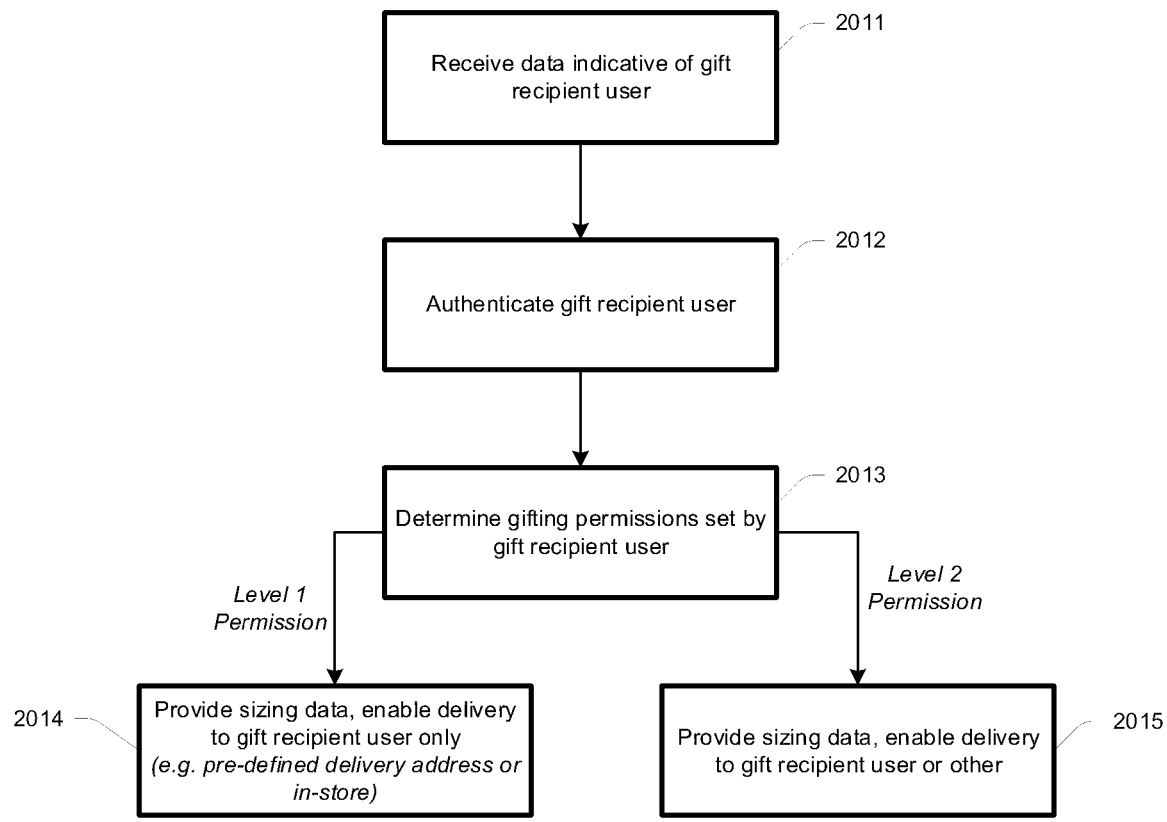

FIG. 2B illustrates a further method, showing receipt of data indicative of a gift recipient user (for example an email address) at 2011, authentication at 2012, and determination of permissions at 2013. Two permissions are considered—a level 1 permission (see 2014) which allows only delivery to the recipient (using a recipient-predefined address) or in-store pickup by the recipient; and a level 2 permission (see 2014) which enables other forms of delivery.

Figure 2C:
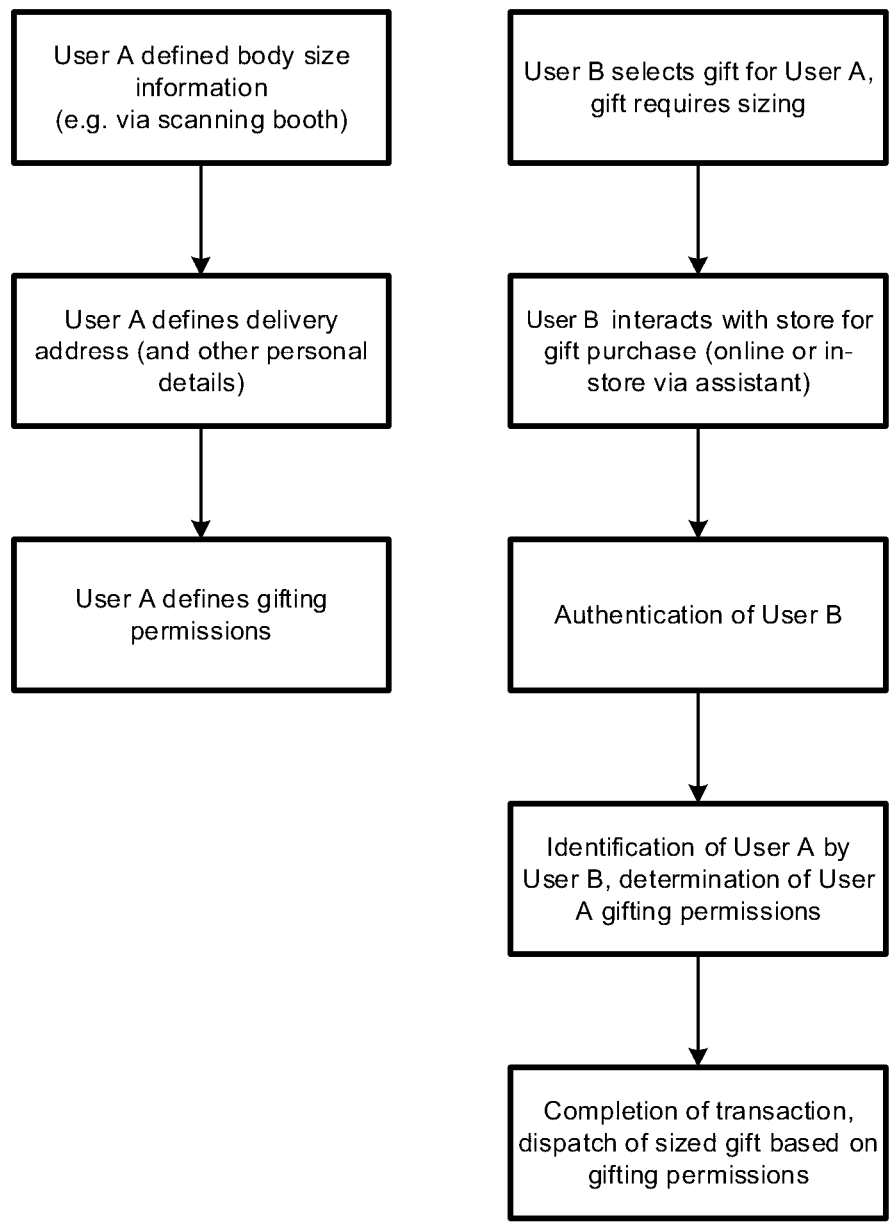

FIG. 2C illustrates a further method, which illustrates both a registration and permission setting process performed by a User A, and a gifting process performed by a User B.

Tracking Progress Against Fitness and Body Transformation Objectives

In some embodiments, scanning booths are implemented as a means for assisting persons in tracking their performance against body goals, for example fitness and body transformation objectives. In broad terms, body scan data from different points in time is compared, thereby to enable presentation of graphical information which accurately shows how a person's body shape has changed.

Various embodiments provide computer implemented methods for enabling tracking of body shape variations. The methods include authenticating a user $U_1$, that user $U_1$ being associated with first user record data, wherein the first user data includes a first set of user physical attribute data associated with a time n ($PAD_1T_n$). The set of physical attribute data is derived from a three-dimensional body scanning process. For example, that data is collected and maintained via scanning booths and server 110.

The methods then include receiving input representative of further set of first user physical attribute data, the further set being associated with a time n+x ($PAD_1T_{n+x}$). For example, a user might return to a scanning booth (or visit another scanning booth) two weeks following a pervious body scanning session.

A computer system is configured to perform analysis of a relationship between $PAD_1T_n$, and $PAD_1T_{n+x}$. This analysis may be performed, for example, at server 110, locally at a scanning booth, at a third party server, or across a combination of two or more of those locations. The method then include providing output configured to enable rendering, at a client device associated with user $U_1$, a graphical object representative of the relationship between $PAD_1T_n$, and $PAD_1T_{n+x}$. For example, the client device may be a mobile device associated with the user, a computer operated by the user, or a scanning booth at which the user is present (for example the user is provided with the output following scanning).

In some embodiments each set of three dimensional body scan data includes a three dimensional point cloud, and analysis of relationships between $PAD_1T_n$, and $PAD_1T_{n+x}$ is based on comparison of the respective point clouds. For example, comparison of the point clouds includes utilisation of vector mathematics to determination spatial variations between corresponding points.

In some embodiments the graphical object is defined based on an overlay of the point cloud for $PAD_1T_{n+x}$, with respect to the point cloud at $PAD_1T_n$. The graphical object need not be displayed as point cloud data; it is preferably a stylised rendering of a human body shape in three dimensions, preferably with transparent characteristics thereby to enable visualisation of variations between $PAD_1T_n$, and $PAD_1T_{n+x}$.

The graphical object preferably provides visual indicators representative of variations between $PAD_1T_n$, and $PAD_1T_{n+x}$. For example, the visual indicators include colours. This may be a region of colour in an object which indicates a region of variation between overlaid three dimensional models derived from $PAD_1T_n$, and $PAD_1T_{n+x}$ respectively. In some cases a first visual indicator (for example red colouring) is used to identify an increase in localised body size, and a second visual indicator (for example blue colouring) is used to identify a decrease in localised body size. As a more advanced arrangement, in some cases a first visual indicator is used to identify an identified improvement towards a predefined body goal, and a second visual indicator is used to identify regression away from the predefined body goal. The predefined body goal may include fat reduction (or a specific aspect of fat reduction) or muscle gain (or a specific aspect of muscle gain). It will be appreciated that muscle gain will typically involve an increase in local body dimensions, whereas fat loss would typically involve a reduction. In some embodiments an algorithm is configured to autonomously predict whether a given variation is a result of fat loss or muscle gain, allowing for automated categorisation of a variation as being "good" or "bad".

The comparison process may be driven through scanning booths themselves, through server 110, or, as shown in n the example of FIG. 1B, via a third party platform 180. Platform 180 includes a fitness objective data input interface, which enables a user (for example via a user interface rendered at a client device) to input data representing a fitness objective, for example fat reduction or muscle increase. A scan data analysis engine causes the comparison of scan data, either at server 110 or (in some embodiments) by instructing that the processing be performed at server 110. A graphical object generator module 108 is configured to deliver, to a user's client device, data to enable rendering of a graphical object that shows body shape variation as described above.

Figure 2D:
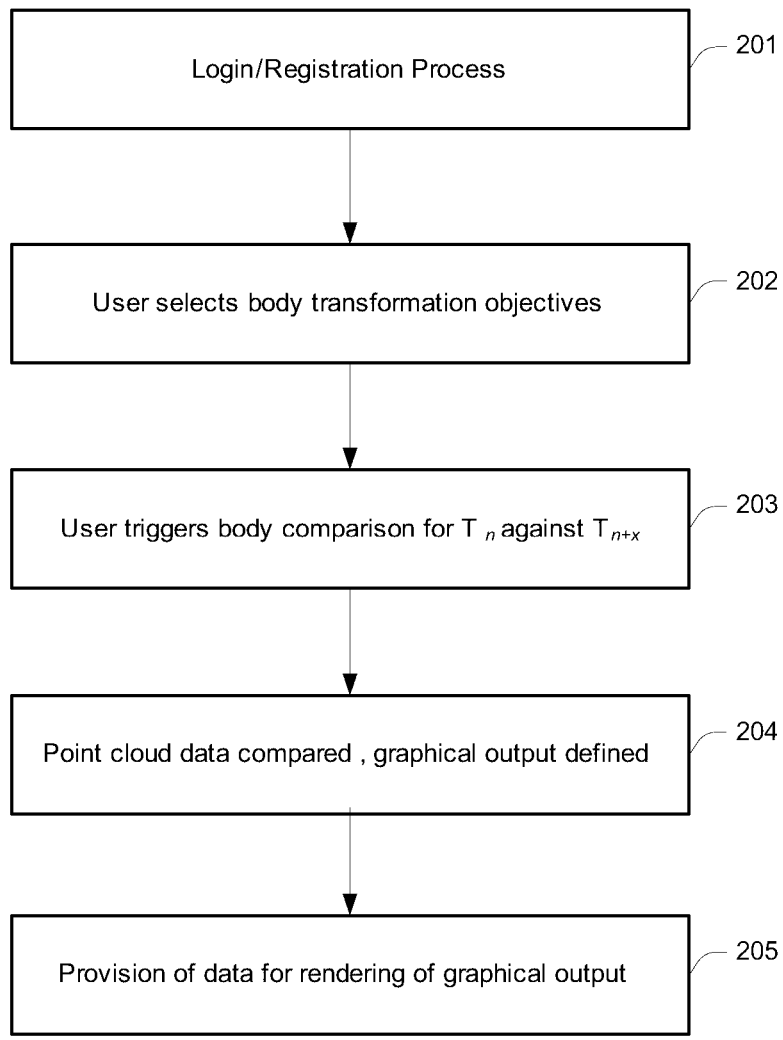

FIG. 2D illustrates a method according to one embodiment. Functional block 201 represents a login/registration process, whereby a user registers to enable tracking of body shape variations. This process provides permissions for the user's body scan data (maintained by server 110) to be accessed for such a purpose. The user then selects body transformation objectives at 202 (this step is omitted in some cases), for example "fat loss", "muscle gain", or in some cases more precise objectives (for example quadriceps muscle growth"). Functional block 203 represents a process including user triggering of a body comparison for $PAD_1T_n$, and $PAD_1T_{n+x}$. This may result from an explicit instruction, or from an implicit instruction 9 for example derived from a user obtaining a new body scan at a scanning booth). Functional block 204 represents a process including comparison and analysis of point cloud data, resulting in defining of graphical output. Data to enable rendering of that graphical output is provided at 205.

Figure 2E:
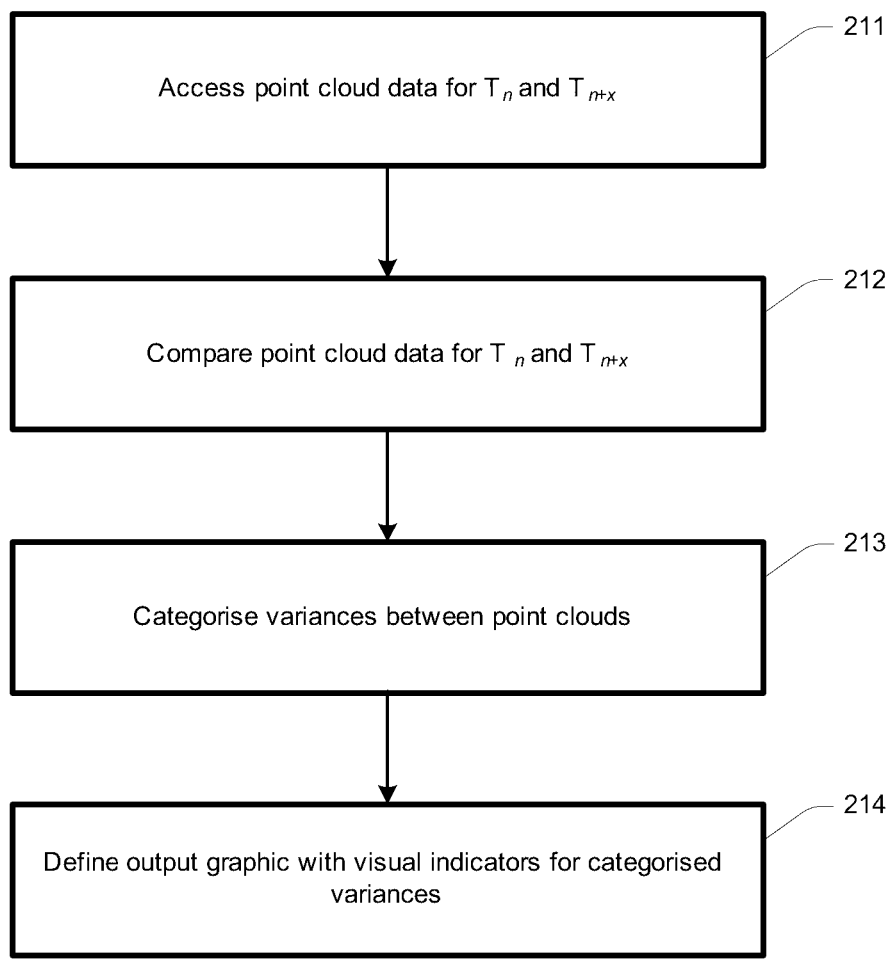

FIG. 2E illustrates a method according to a further embodiment. Functional block 211 represents a process including accessing, from server 110, point cloud data for $PAD_1T_n$, and $PAD_1T_{n+x}$. Functional block 212 represents a process including comparing point cloud data for $PAD_1T_n$, and $PAD_1T_{n+x}$. Functional block 203 represents a process including categorising variances (for example size increase/decrease, movement towards/away from objective, etc). Functional block 203 represents a process including defining an output graphic based on the categorisation.

Fitness Objective Oriented Matchmaking

In some embodiments, the collection of 3D body scan data supports matchmaking based on a combination of fitness objectives, which are defined by a user, and physical attributes, which are objectively determined via body scan data. In some examples, this may be used by a business (for example a personal trainer) wishing to identify a particular person or persons for the purpose of marketing tailored fitness regimes (which are tailored to persons having particular similar objectives and similar body types). In other cases, such as those described in detail further below, this is used to enable users to identify training partners with similar fitness objectives and similar body types.

FIG. 1B illustrates an embodiment where the framework of FIG. 1A is implemented in the context of a matchmaking arrangement. In this example, a fitness service platform 180 takes the place of a third party platform 130 in FIG. 1A. It will be appreciated that some or all functionalities of platform 180 may be integrated into server 110. Three functional components are illustrated:

A fitness objective input interface 181. This enables a user to define fitness objectives (for example body transition objectives), as discussed further below. There may be additional input interfaces which enable defining of other personnel data (for example age, location, fitness level, etc.).

A matchmaking engine 182. This is configured to identify user-user matches. In the present example, these are bidirectional matches, in the sense that a first user $U_i$ meets criteria set by a second user $U_j$, and the second user $U_j$ meets criteria set by the first user $U_i$. The matchmaking engine identifies matches based on factors including body scan data provided by server 110, as discussed in detail below.

A user-user interaction platform 183, which enables communication between users $U_i$ and $U_j$ subject to the identification of a bidirectional match between users $U_i$ and $U_j$.

Some embodiments provide a computer implemented method for enabling identification of users based on a combination of fitness objectives and physical body characteristics. The methods include authenticating a user $U_1$ at a server device, the user $U_1$ being associated with first user record data, wherein the first user data includes user physical attribute data $PAD_1$. This physical attribute data is derived from a three-dimensional body scanning process as described above.

An interface is provided to the user, this interface being configured to enable a user $U_1$ to define fitness objective data $FOD_1$. The fitness objective data may include any one or more of the following:

Objectives defined by reference to fitness challenges (for example training for an event, increasing cardiovascular abilities, increasing flexibility, commencing from a low level of previous activity, recovering from an injury, etc).

Objectives defined by reference to activity types (for example jogging, tennis, training for snowsports, weight training, and so on).

Objectives defined by reference to body transformation (for example building muscle, toning particular muscle groups, weight loss, weight loss in specific body reasons, and so on).

The methods then include associating the defined fitness objective data $FOD_1$ with the first user $U_1$ in an information system, wherein the information system maintains, for a plurality of users $U_1$ to $U_n$, and physical attribute data $PAD_1$ to $PAD_n$ and fitness objective data $FOD_1$ to $FOD_n$.

A comparison algorithm is executed in respect of data maintained by the information system, wherein the comparison algorithm is configured to identify relationships between a given user $U_i$ and a given user $U_j$ based on a combination: (i) threshold similarity between $FOD_i$ and $FOD_j$; and (ii) threshold similarity between of $PAD_i$ and $PAD_j$.

The information system may span multiple locations and/or platforms. For example, in some embodiments comparison of FOD is performed at a first server, which is part of a fitness service management platform, and comparison of FOD accord at a server such as server 110. In some embodiments all comparison processes are performed at server 110.

The comparison algorithm varies between embodiments. Exemplary functionalities include:

Enabling a business user to identify a group of normal users, for example to market training services (that is, providing an interface configured to allow input of target user criteria based on a combination of FOD and PAD; and subsequently providing an output representative of a set of users identified as satisfying the target user criteria).

Enabling users to identify other users who share similar fitness objectives, and share similar body type characteristics (that is, providing to user $U_1$ data representative of a set of one or more complementary users from $U_2$ to $U_n$ based on relationships identified by the comparison algorithm).

In the case of user-user matching, in some cases, for each of the complementary users, the method includes providing to $U_1$ data representative of suggested collaborative fitness goals. For example, one set of users is suggested as "users who would be good jogging partners for you", another as "these users are looking for weight training partners, and would be suited to you" or "these users share similar body transformation objectives".

The matching preferably additionally incorporates further criteria, including the likes of location, age, fitness level, and so on. That is, whilst PAD and FOD are key parameters, they need not be the sole parameters for user-user matching. For instance, in one embodiment the comparison algorithm additionally accesses and utilises, for each user $U_1$ to $U_n$, current fitness level data $CFD_1$ to $CFD_n$. Each user's respective CFD is preferably determined from an interactive survey process.

In embodiments where PAD is derived from a three dimensional body scan, users are able to track progress against goals (for instance against a particular body characteristic transformation objective) by way of repeated collection of body scan data. That is, a user periodically visits a body scanning booth, and this allows fitness service platform 180 to provide reports on progress, including in some cases progress against goals.

Figure 2F:
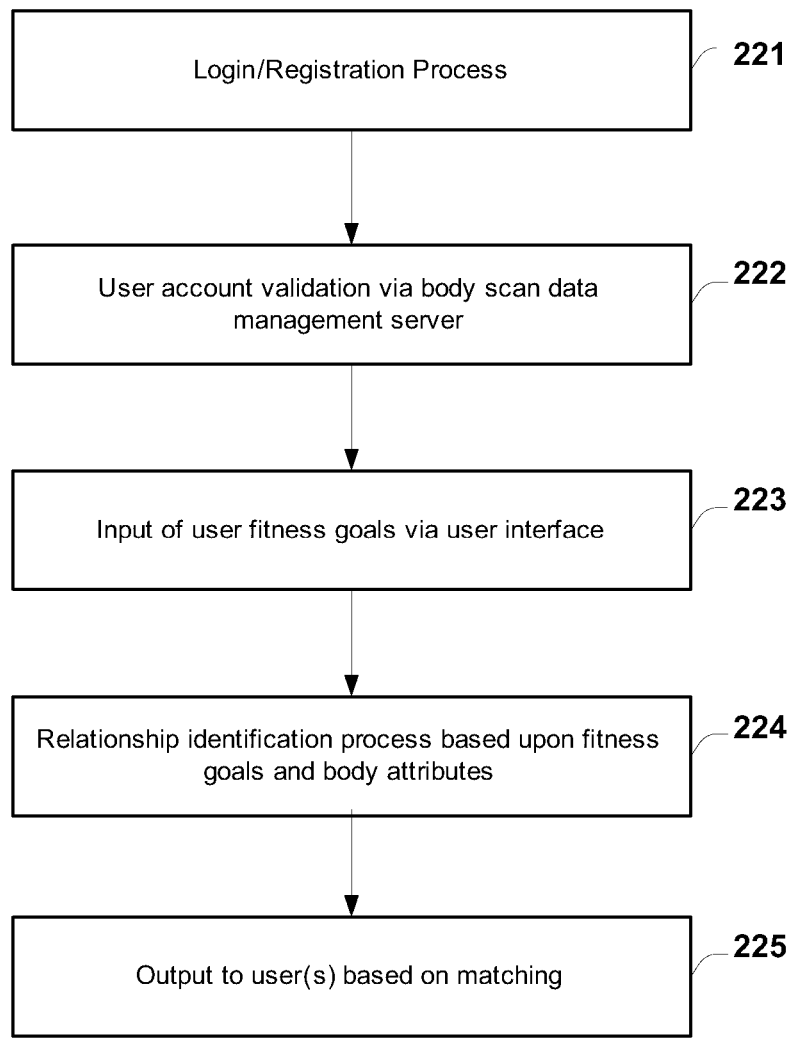

FIG. 2F illustrates a method according to one embodiment. Functional block 221 represents a login/registration process, whereby a user registers to use fitness service platform 180. As part of registration, or following registration, a user account verification is performed with server 110 at 222, thereby to determine that necessary body scan data is available (for example in some cases a user must provide authority for platform 180 to access such data from server 110). A user input fitness objective data at 223, and a relationship identification process follows at 224. Users are informed of the outcome of the relationship identification process at 225.

Figure 2G:
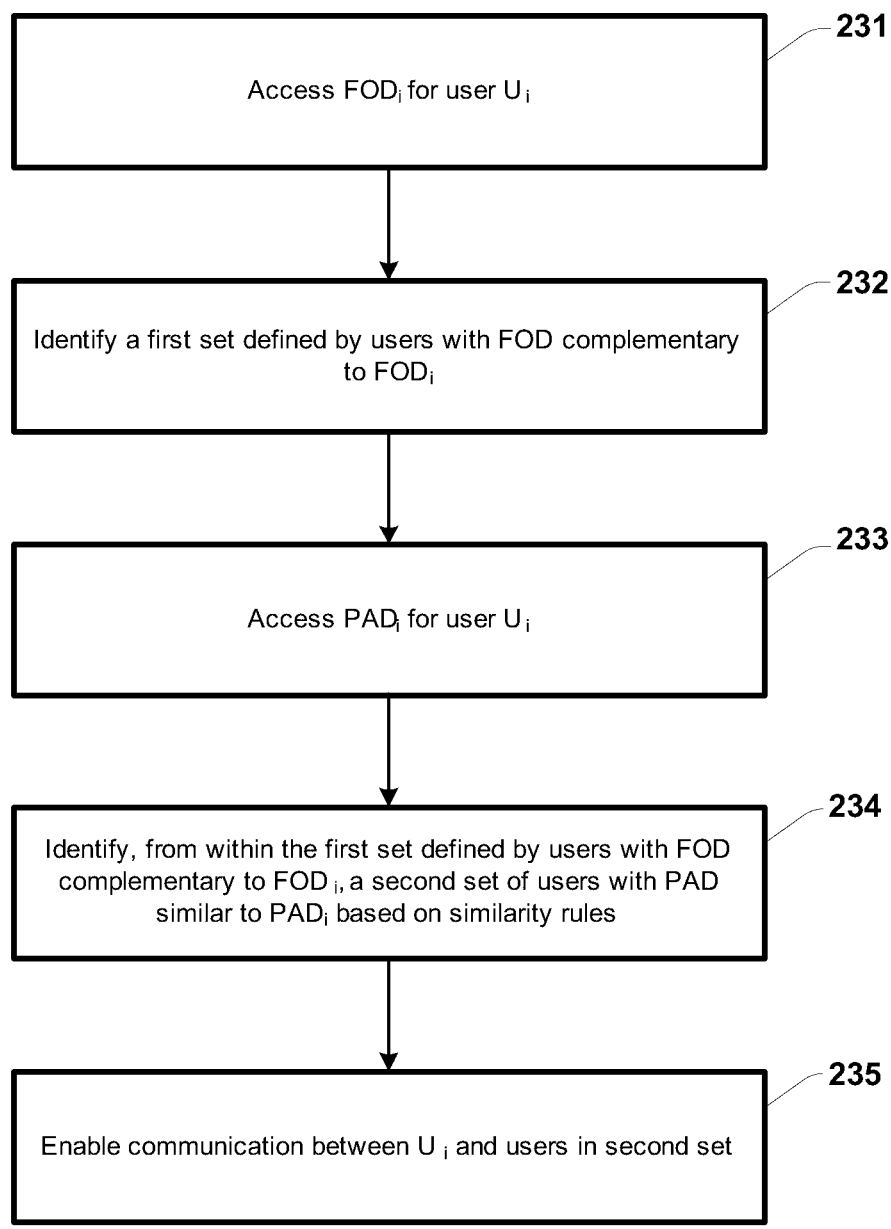

FIG. 2G illustrates an exemplary relationship identification process according to one embodiment. This is described by reference to a user $U_i$, who has defined $FOD_i$. Functional block 231 represents a process including accessing $FOD_i$ for $U_i$. Functional block 232 represents a process including a first set of users having respective FODs that are complementary with $FOD_1$. The method then includes, at 233, accessing $PAD_i$ for user $U_i$. At 234, the method includes identifying, from within the first set defined by users with FOD complementary to $FOD_i$, a second set of users with PAD similar to $PAD_i$ based on similarity rules. The similarity rules define what it means for two bodies to be "similar", and the rules may be specific to fitness objectives (for example certain objectives may require users to be of similar heights, whereas other objectives may look for users with similar levels of midsection body fat).

Functional block 235 represents a process including enabling communications between user $U_i$ and users in the second set (and vice-versa).

Matchmaking Overview

In some embodiments, the collection of 3D body scan data supports matchmaking based on physical attributes that are able to be objectively determined via body scan data. In some examples, this may be used by a business wishing to identify a particular person (or persons) meeting desired body type/shape requirements, for example in the context of recruiting for acting or modelling roles. In other cases, such as those described in detail further below, this is used to provide or supplement matchmaking in the context of person-person relationships (for example in the context of dating).

In general terms, embodiments include methods including: (i) providing an interface configured to enable a first user to define data representative of desired physical attributes; (ii) accessing a database of physical attributes for a plurality of further users, the physical attributes being derived from three-dimensional body scanning; and (iii) providing output indicative of one or more of the further users for which their respective physical attributes satisfy the desired physical attributes, based on predefined satisfaction rules.

The predefined satisfaction rules define what it means to satisfy particular desired physical attributes. These vary between embodiments, for instance based on the level of specificity with which desired physical attributes are defined. The following examples are provided as context:

In some embodiments, a plurality of body types are defined, for example "athletic", "petite", "curvy" and so on, and each user for whom body scan data is held is automatically categorised into one of those body types based on characterisation rules.

In some embodiments, a much more specific approach is implemented, whereby a user is able to define desired characteristics for particular physical attributes (for example one or more of height, chest characteristics, general shape characteristics, arm characteristics, and so on) and the rules determine whether another user's body scan data is sufficiently similar to the defined desired attributes to warrant a match.

In some cases matches are absolute (match/no match), in other cases matches are defined based on the extent of similarity (for example a 100% match, a 60% match, and so on).

Matchmaking Framework

FIG. 1B illustrates an embodiment where the framework of FIG. 1A is implemented in the context of a matchmaking arrangement. In this example, a matchmaking platform 180 takes the place of a third party platform 130 in FIG. 1A. It will be appreciated that some or all functionalities of platform 180 may be integrated into server 110. Three functional components are illustrated:

A desired physical attribute input interface 181. This enables a user to define desired physical attributes for the purpose of matchmaking, as discussed further below. There may be additional input interfaces which enable defining of other matchmaking desire data (for example age, location etc.) as is customary in prior art matchmaking engines. However, those are omitted for the sake of simplicity in the current example.

A matchmaking engine 182. This is configured to identify user-user matches. In the present example, these are bidirectional matches, in the sense that a first user $U_i$ meets criteria set by a second user $U_j$, and the second user $U_j$ meets criteria set by the first user $U_i$. The matchmaking engine identifies matches based on factors including (or solely based on) body scan data provided by server 110, as discussed in detail below.

A user-user interaction platform 183, which enables communication between users $U_i$ and $U_j$ subject to the identification of a bidirectional match between users $U_i$ and $U_j$.

Although examples are described by reference to bidirectional matching (which is particularly relevant in the context of a relationship matchmaking engine (for example in the context "dating" services and the like), as noted above some embodiments identify unidirectional matches. Such unidirectional matching finds application where a given user (for whom body scan data might not be defined) wishes to identify one or more persons based on physical attributes derived from their body scan data. For example, this is potentially useful in the context of identifying persons for modelling roles, acting roles, sporting selections, and so on.

Bidirectional Matchmaking Methodologies

Some embodiments provide computer implemented method for enabling user-user matching in a bidirectional manner, for users who make use of 3D body scan data maintained by server 110. The methods preferably include, in respect of an exemplary user, authenticating a first user (referred to as $U_1$) at a server device, the user $U_1$ being associated with first user record data (provided by server 110), wherein the first user data includes user physical attribute data $PAD_1$, this physical attribute data being derived from a three-dimensional body scanning process.

The methods then include providing, to $U_1$, an interface configured to enable the first user to define data representative of desired physical attributes $DPA_1$. The nature of the interface varies between embodiments, and examples are provided further below. The defined data representative of desired physical attributes $DPA_1$ is associated with the first user $U_1$ in an information system. This is an information system that maintains, for a plurality of users $U_1$ to $U_n$, and physical attribute data $PAD_1$ to $PAD_n$ and desired physical attribute data $DPA_1$ to $DPA_n$. The information system may in some embodiments be spread across multiple distributed locations and/or platforms.

The methods include executing a matching algorithm in respect of data maintained by the information system, wherein the matching algorithm is configured to identify a user-user match for a given user $U_i$ and a given user $U_j$ in the case that:

(i) the matching algorithm identifies $PAD_j$ as satisfying $DPA_i$; and (ii) the matching algorithm identifies $PAD_i$ as satisfying $DPA_j$.

That is, the matching algorithm identifies bidirectional matches where each user party to the match meets criteria defined by the other user. The method then includes providing output representative of the user-user match for users $U_i$ and $U_j$. The nature of that output varied depending on design of the matchmaking platform, and in some embodiments includes an output that enables communication between the matched users.

Although examples described herein describe physical attributes as a sole parameter for matchmaking, various embodiments use physical attributes as one of a plurality of matchmaking parameters (with others including the likes of age, location, vocation, and so on).

Figure 2H:
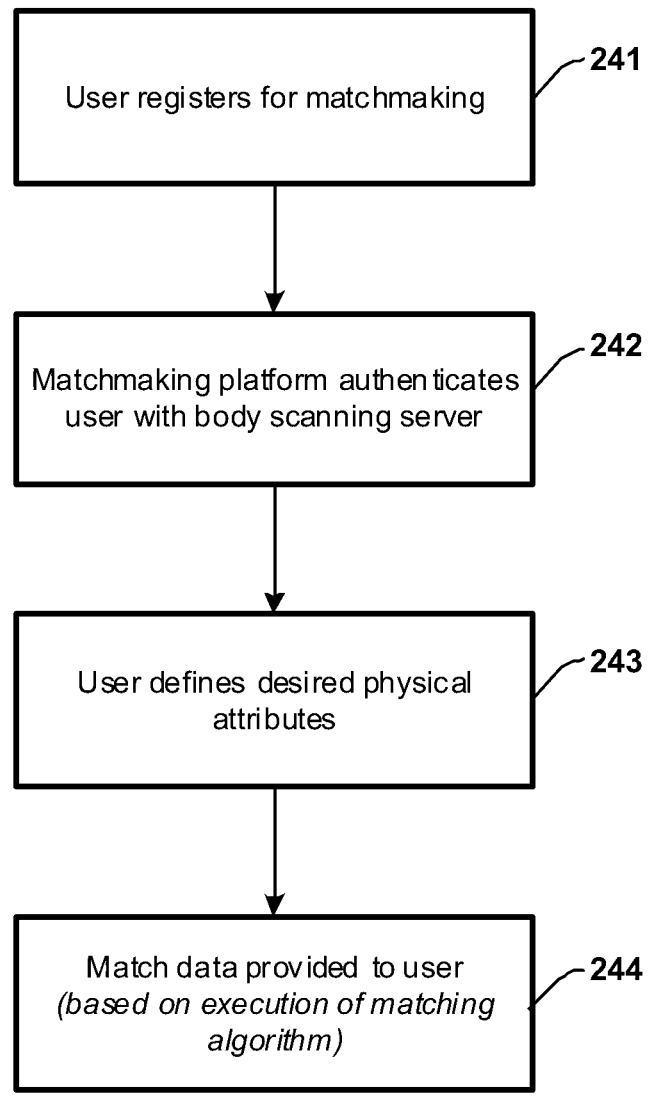

FIG. 2H illustrates a method according to one embodiment. In this method, a user registers for matchmaking at 241. At 242, the matchmaking platform authenticates with the body scanning server, thereby to validate that necessary body scan data is available for matchmaking purposes. In some embodiments, this leads to a further process whereby the user's body scan data is processed to define additional data sets that are configured to be utilised to the purpose of assessing the user's PAD against a given set of DPA.

At 243, the user defines desired physical attributes, for example using an interface as described further below. Then, subject to executing of the matching algorithm, match data is subsequently (and in some embodiments on an ongoing basis) provided to the user at 244.

Figure 2I:
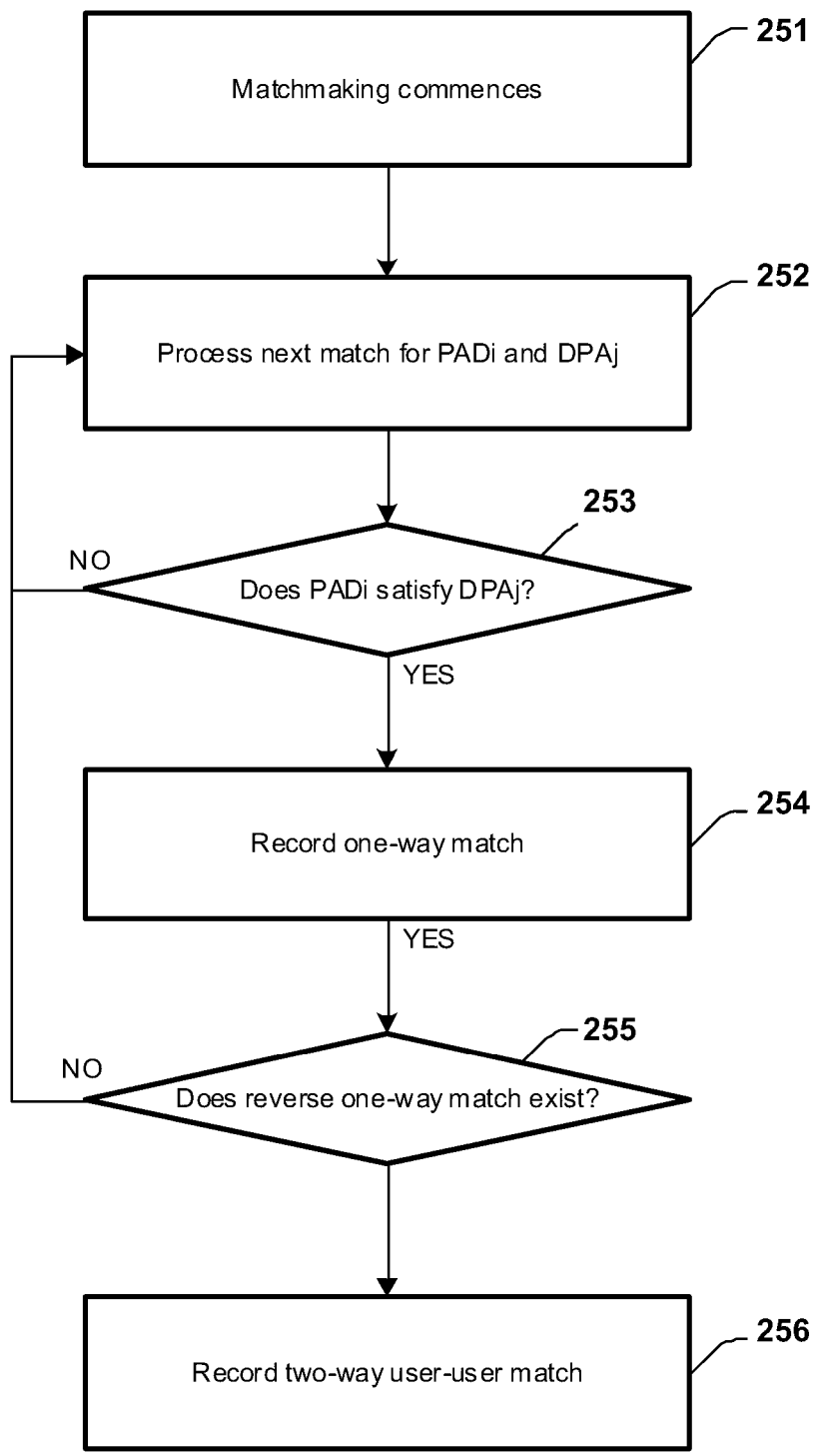

FIG. 2I illustrates an exemplary bidirectional matchmaking process. It will be appreciated that various alternate bidirectional matchmaking processes are used in further embodiments. Matchmaking commences at 251, for example the matchmaking engine commences operation. At 252 the engine processes a next unique combination of $PAD_i$ and $DPA_j$, and determines (at decision 253) whether $PAD_i$ satisfies $DPA_j$. If rules for satisfaction are satisfied (which may include a threshold level of similarity overall, or a threshold level of similarity for one or more individual physical attributes), a one-way match is recorded at 254, this being a match of $U_i$ to $U_j$. Otherwise, the method loops to 213.

Following 254, decision 255 includes determining whether the reverse one-way match has already been recorded (that is, a match of $U_j$ to $U_i$). If such a match exists, a bidirectional match is recorded at 256, which triggers other activities within the matchmaking platform. Otherwise, the method loops to 252.

Each time an entry of PAD or DPA is added/modified, it is returned for processing via new unique combinations. In some embodiments, a given user is able to define multiple sets of DPA, and have those processed for matches in parallel.

Defining Desired Physical Attributes

As noted above, in the context of defining desired physical attributes:

In some embodiments, a plurality of body types are defined, for example "athletic", "petite", "curvy" and so on, and each user for whom body scan data is held is automatically categorised into one of those body types based on characterisation rules.

In some embodiments, a much more specific approach is implemented, whereby a user is able to define desired characteristics for particular physical attributes.

In relation to the latter, in come embodiments, given user $U_i$, $DPA_i$ is representative of a plurality of individual attribute criteria (for example one or more of height, chest characteristics, general shape characteristics, arm characteristics, and so on). An interface enables user to make selections and define desired values for each of the individual attribute criteria. By way of example, some embodiments implement an approach whereby the interface configured to enable the first user to define data representative of desired physical attributes $DPA_1$ enables a user to select one of a plurality of individual attribute criteria, for that selected criteria select a body type, and for that body type select an intensity value. For instance, a user selects "arms", then selects "muscular", and then sets a value for the level of muscularity. In some cases, the interface enables a user to assign relative importance ratings to one or more of the individual attribute criteria (for example setting "high" importance to defined height values, and "low" importance to defined arm muscularity values). In some embodiments interface configured to enable the first user to define data representative of desired physical attributes $DPA_1$ enables a user to define tolerances and/or ranges for one or more aspects of $DPA_1$.

In some cases, a first one of the individual attribute criteria is linked by a proportionality relationship to a second one of the individual attribute criteria. For example, values for arm girth are linked to arm length. In some cases one or more the individual attribute criteria are proportionally scalable relative to a height parameter.

Figure 4A:
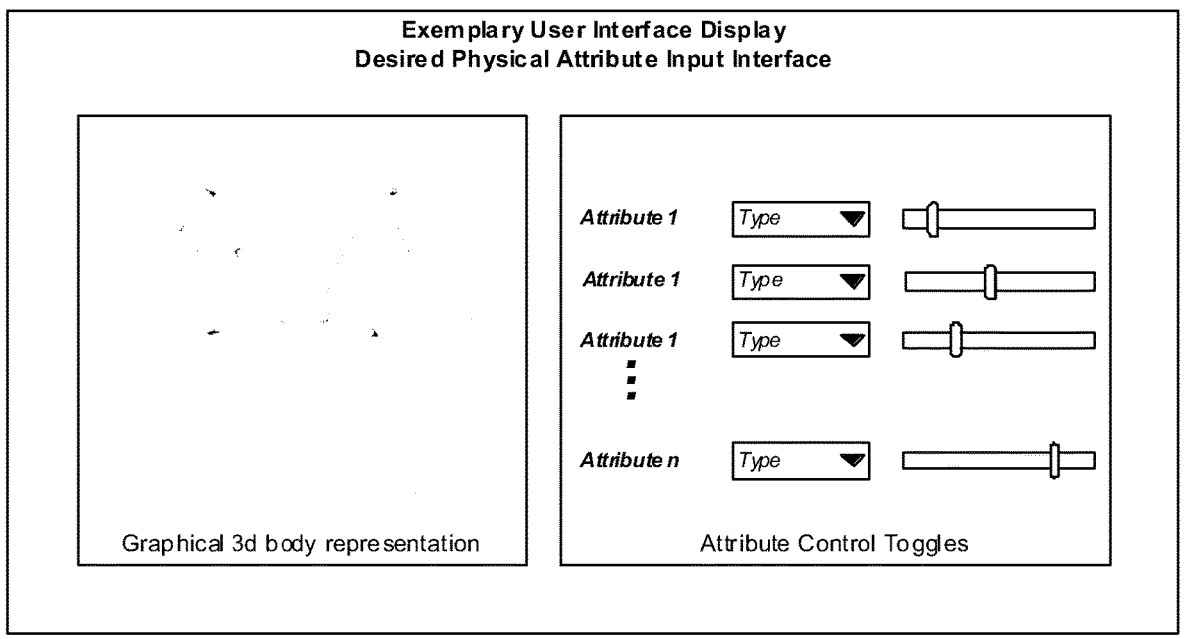
FIG. 4A illustrates an exemplary user interface display.

In preferred embodiments, the interface configured to enable the first user to define data representative of desired physical attributes $DPA_1$ includes a user interface component that provides a graphical representation of $DPA_1$. For instance, the graphical representation includes a body shape graphic, such as a three-dimensional graphical object (i.e. a graphic that can be viewed from multiple virtual viewpoints).

Where a graphic is provided, in some embodiments the interface includes a component that enables the user to define aspects if $DPA_1$ via manipulation of the graphical representation. For example, the user is able to directly manipulate the graphic (by moving control points) thereby to define a desired body shape. In some cases, control toggles external to the graphic are provided, and the graphic updated in real time responsive to manipulation of the control toggles. One such example is illustrated in FIG. 4A, which shows a plurality of attribute control elements, each including a "type" selection component (shown as a drop down menu) and an intensity selection component (shown as a slider), and as these are manipulated a body graphic on the left is updated accordingly.

The matching algorithm is configured to apply a predefined protocol thereby to determine whether a given $PAD_i$ satisfies a given $DPA_j$. The predefined protocol preferably operates in a distinct manner of each of a plurality of individual attribute criteria (rather than a common numeric manner). That is, particular rules are defined for assessing whether DPA data for arms are satisfied by particular PAD representative of the user's arms.

Exemplary Measurement-Based Promotional Methods

In some embodiments, a proximity-based matching algorithm is applied thereby to identify vendors and/or specific garments proximal a user (based on mobile device location, assessed using GPS or other means) based upon their body scan data and/or other parameters. This is preferably used thereby to assist a user in identifying garments suitable for their size in nearby locations, in some cases limited to garments for which special prices or the like are being offered. This, in some embodiments, is based upon matching of fit parameters provided by vendors and sizing data determined for a given user.

In some embodiments this algorithm is applied via a mobile app, for example thereby to provide a "Find clothes nearby" functionality. Recommendations may be filtered by brand, colour, price, discount, and/or other parameters.— Recommendations may will take into account factors including but not limited to Previous purchases;
Purchases made by people of similar measurements; and
Purchasing preferences indicated by the user.

In further embodiments proximity-based matching is implemented in broader context, for example in relation to health/fitness applications as opposed to clothing sizes.

Marketing Based on Size, Including Overstock Marketing

In some embodiments, technologies discussed herein are implemented thereby to enable marketing based on consumer size. A particular example of this is overstock marketing, where a vendor has a surplus of items in a particular size.

One embodiment provides a computer implemented method for configured to provide vendors access to potential customers based on customer size information, the method including: maintaining access to a database including data representative of consumer body dimension attributes, wherein the data is derived from 3-dimensional body scans; receiving a request from a vendor, wherein the request is indicative of desired consumer body attributes, wherein the desired body attributes correspond to appropriate sizes for a set of one or more products to be marketed; identifying, in the database including data representative of consumer body dimension attributes, a set of one or more consumers satisfying the desired body attributes; and providing data representative of the set of one or more consumers.

In some embodiments, the method includes providing data representative of the set of one or more consumers to the vendor, which may allow the vendor to provide specific marketing materials.

In some embodiments the method includes providing data representative of the set of one or more consumers includes providing data thereby to enable filtering of web page information rendered at a client terminal associated with a given consumer, such that the given consumer is enabled only to view predetermined data relating to the set of one or more products to be marketed in the case that the given consumer belongs to the set of one or more consumers. For example, a consumer performs a body-scan server associated authentication process at a vendor website. In the case that the vendor has subscribed to a marketing plan which includes identification of users having body attributes corresponding to that consumer, the website automatically configures to make visible to the consumer specific size-appropriate goods. This is useful in clearing overstock clothing in specific sizes; a vendor may subscribe to users having body sized appropriate to that clothing, thereby to streamline the process of marketing (and ideally selling) the relevant garments.

Another embodiment provides a computer implemented method for configured to provide vendors access to potential customers based on customer size information, the method including: Identifying a set of products to be marketed via on online marketplace, wherein the set of products as associated with common sizing parameters; determining a set of body attributes associated with the common sizing parameters; Identifying, in a database including data representative of consumer body dimension attributes, wherein the data is derived from 3-dimensional body scans, set of one or more consumers having the determined body attributes; and providing data thereby to enable display of the set of products, via the online marketplace to only the set of one or more consumers. Again, this may be subscription based, such that a marketing premium paid by a vendor is related to one or more of (i) a range of body sizes; (ii) a number of consumers falling into a desired body size range; and (iii) a number of ranges of body sizes.

Product Sizing Recommendations Via Mobile Devices

Some embodiments provide computer implemented methods for enabling delivery of product sizing information via mobile devices. This is described by reference to FIG. 2J and FIG. 4B. Embodiments are described by reference to sizing information for wearable garments, for example clothing items. However, it should be appreciated that the technology is equally applicable to various other products where the product comes in multiple sizes (or is able to be sized) specifically for a user. Examples include sporting equipment (such as golf clubs and bicycles), furniture (such as office chairs), and so on.

In terms of a mobile device method, one embodiment includes inputting, via the mobile device, data representative of a product, in this case being a garment. The method then includes transmitting, from the mobile device to a server, (i) data representative of the garment; and (ii) data configured to enable authentication of a user of the mobile device. The server then performs a process thereby to determine user-specific garment sizing information for the garment, which is transmitted to the mobile device. The mobile device renders, via a user interface provided by the mobile device, the user-specific garment sizing information for the garment.

Such a mobile device method is in some embodiments performed using a proprietary mobile app executed on the mobile device. However, in other embodiments a web-browser approach is implemented, whereby data that enables rendering of a user interface on the mobile device is downloaded as-required from a web server and rendered in a browser application. It will be appreciated that substantially the same functionalities may be provided via either web-browser or proprietary app approaches.

The data representative of the garment is inputted responsive to a local interaction between the mobile device and the garment. In preferred embodiments the local interaction between the mobile device and the garment includes reading of an identifier carried by the garment. This may be an identifier that is carried by a label (for example a removable label, optionally a label applied by a vendor). The identifier may include a visually readable identifier (such as a barcode, numerical information textual information, or the like), in which case it is preferably read using a camera module provided by the mobile device. Alternately, in some embodiments the identifier includes a wirelessly readable token, for example an RFID tag, BLE tag or the like, in which case it is read using a corresponding reader module provided by the mobile device.

The server is configured to: process the data configured to enable authentication of a user of the mobile device thereby to authenticate the user; and following the authentication, access body sizing information associated with the user. In preferred embodiments, the body sizing information is derived from a 3D body scan, for example wherein the 3D body scan is performed at one or a plurality of networked body scanning booths (as described further above).

In some embodiments the server maintains access to a repository of sizing rules. For example, these sizing rules may include any one or more of the following:

Sizing rules that associate a particular garment type (for example pants, a shirt, etc) with recommended sizes based on one or more measurements/attributes derived from 3D body scan data.

Sizing rules that associate a particular garment type from a particular brand with recommended sizes based on one or more measurements/attributes derived from 3D body scan data. That is, sizing rules may be associated with particular brands.

Sizing rules that associate a particular specific garment with recommended sizes based on one or more measurements/attributes derived from 3D body scan data. For example, sizing information specific to individual garments may be maintained (or maintained in a location accessible to) the server.

The server is configured to access body sizing information associated with the user, and wherein the server is configured to process the data representative of the garment based on the sizing rules and the body sizing information associated with the user thereby to determine the user-specific garment sizing information for the garment.

In some embodiments the server is configured to interact with vendor and/or manufacturer information systems (such as inventory systems) thereby to identify a garment based on data received from the mobile device. In other embodiments the server maintains a database for that purpose.

The user-specific garment sizing information is in some embodiments recommended sizing information, and may include two or more recommended sizes (for example multiple sizes which the user is encouraged to take to a changing room to test). In some embodiments the mobile device additionally provides graphical data simulating garment fit relative to the users body, the graphical data being generated using an avatar defined based on the user's 3D body scan data and image data that provides a 3D virtual representation of the garment (or, in some embodiments, a 2D representation).

Figure 2J:
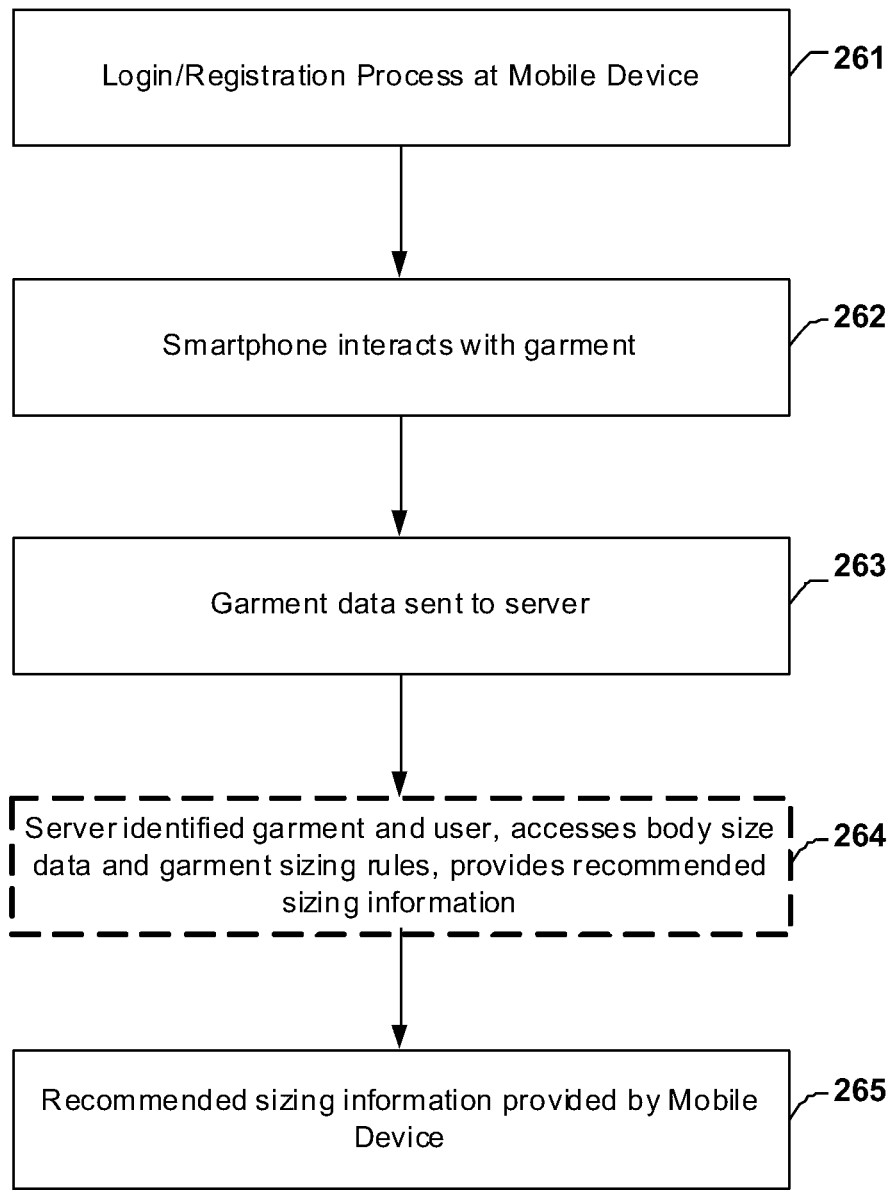

FIG. 2J illustrates a mobile device method according to one embodiment, performed via a proprietary app. Functional block 261 represents a login/registration process, whereby a user inputs information that enables authentication of the user by a server, thereby to enable access to the user's body scan data. This is preferably performed as a one-off operation, such that the app is configured to provide authentication information to the server on an ongoing basis without requiring the user to manually provide authentication data each time.

Functional block 262 represents a process including a smartphone interaction with a garment. This may include image capture via a camera module, either from within the app, or external of the app (in which case the app accesses a stored image file). The image data may be of the garment, a garment label, barcode, or the like, depending on how the embodiment is practically implemented. Alternately, as noted above, a wireless tag reading process may be performed. This results in the generation of garment data, which is transmitted to the server at 263. The server then determines recommended sizing information based on (i) one or more attributes determined from the garment data; (ii) sizing rules; and (iii) one or more data attributes derived the user's body scan data at 264. This recommended sizing data is provided to the user via the mobile device at 265.

Figure 4B:
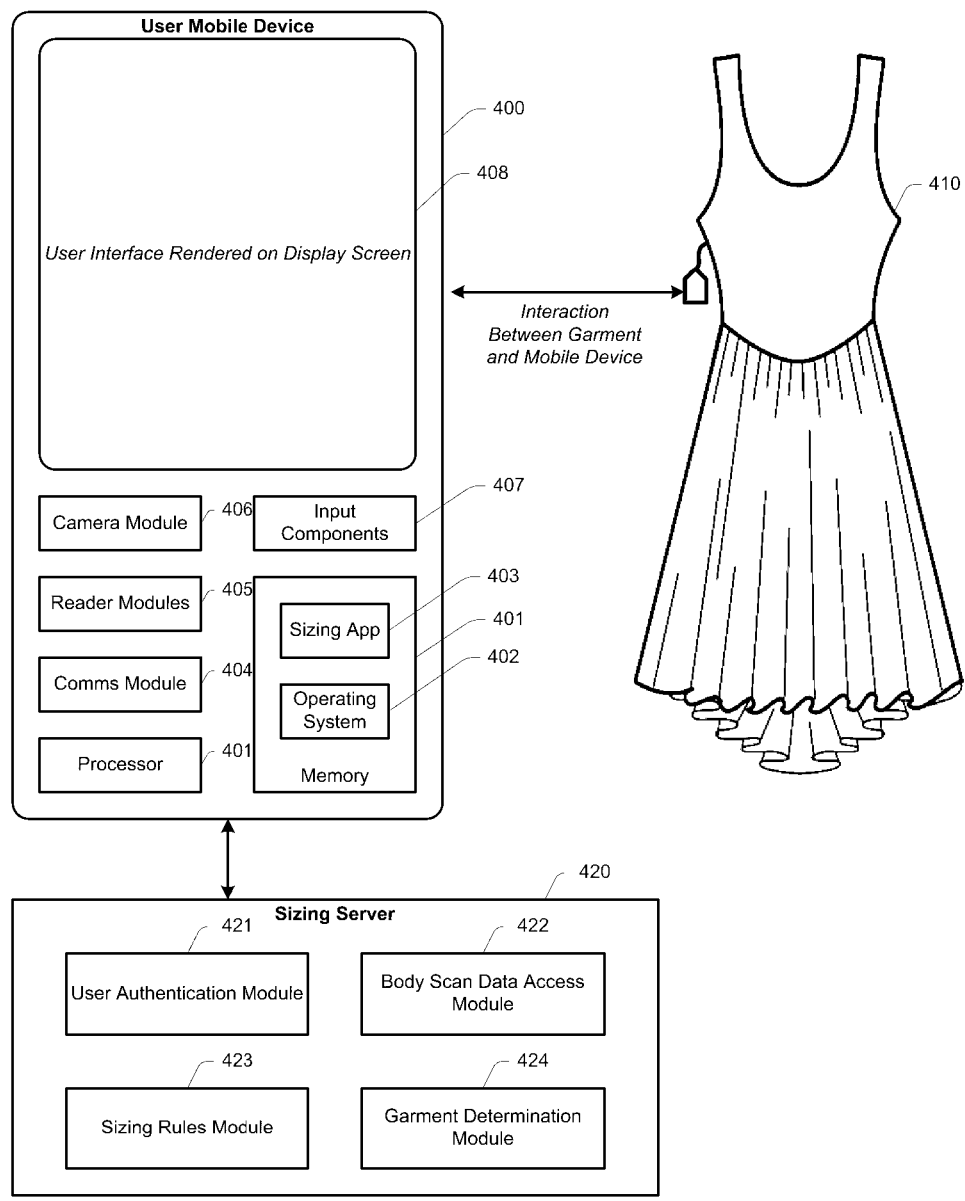
FIG. 4B illustrates an exemplary mobile app arrangement.

FIG. 4B illustrates an arrangement according to one embodiment whereby a user mobile device 400 locally interacts with a product in the form of a garment 410, and obtains recommended sizing information from a sizing server 420 (which may be provide via, or in communication with, a server such as server 110 of FIG. 1A.

Mobile device 400 includes a processor 401 coupled to a memory module 402. Memory 402 maintained computer executable code to enable execution of an operating system 403 and a sizing app 402. A comms module 405 (which may include cellular, WiFi and/or other forms of communications module) enables the sizing app to communicate with sizing server 420. Mobile device 400 additionally includes reader modules (which may include RFID readers, Bluetooth, and so on), which enable reading of wireless tokens that may be provided by garment 410, and a camera module 407 that enables reading of visually recognisable identifiers. A display screen 408 renders a user interface provided by app 404, and input components 409 (for example including a touchscreen, buttons and a microphone) enable the user to interact with the app.

Server 420 includes a user authentication module, which is configured to enable authentication of a user based on data provided by mobile device 400. This enables a body scan data access module 422 to access body scan data associated with the user. A garment determination module 424 is configured to determine garment information/attributes based on data derived from an interaction between mobile device 400 and garment 410. The garment information/ attributes and body scan data are processed based on sizing rules provided by a sizing rules module 423 thereby to determine user-specific garment sizing information, which is communicated by server 420 to mobile device 400.

Integration Between Body Scan Management Framework and Video Games

In some embodiments, third party platforms 130 include one or more video game servers, which are each configured to interact with client terminals that are used by video game players to play video games. These may include console video games, mobile games, PC games, and so on. The game may be played based on a combination of local data maintained at the client terminals and centralised data made available by a server (which may be the video game server). However, regardless of where underlying game data and logic is executed, each client terminal provides a local graphical rendering of the video game being played by a user. In overview, body scan data is used to enable the generation of personalised graphical objects, such as in-game characters that closely reflect body attributes of the player.

Some embodiments provide computer implemented methods for managing body scan data, such as methods performed via operation of server 110. These methods include maintaining access to a repository of body scan data, wherein the repository of body scan data includes a plurality of sets of body scan data derived from respective body scanning processes performed at distributed scanning booths, and maintaining access to a user record database, wherein the user record database includes user data records for a plurality of users, wherein each user data record is associated with one or more sets of body scan data.

The methods additionally include providing a video game interface module, the video game interface module being configured to perform a data exchange with a plurality of video game servers. For example, each video game server is associated with a respective one or more games. The data exchange enables body scan data for a given user to be shared to the video game server, which transforms that body scan data to define a personalised virtual object representative of the user.

In some embodiments the data exchange includes delivery to a particular video game server of a set of body scan data associated with a user $U_1$ in the user record database in response to authentication of user credentials associated with user U1 in the user record database, wherein the user credentials are transmitted via the video game server. For example, a user interacts with a given video game using his/her client terminal, and selects a user interface option relating to generating a personalised character. This prompts the user to input user credentials associated with a body scan management server, thereby to enable a video game server to request and obtain, from the body scan server, body scan derived data that is required to enable defining of the relevant personalised character.

In some embodiments the data exchange includes delivery to a particular video game server of a set of body scan data associated with a user U1 in the user record database in response to authentication of user credentials associated with user U1 in a record database associated with the video game server, wherein the user credentials are transmitted via a scanning booth (or another user interface device that interacts with server 110). For example, the scanning booth provides a user interface that enables a user to select a video game associated with the video game server, and input of user credentials associated with a user $U_1$ in a record database associated with the video game server. As context, in some embodiments a video game user is registered with one or more online game services, for example services that provide access to online gaming and the like. By providing credentials for one or more of those registrations to server 110, a video game server is enabled to identify to server 110 using its own known user credentials, thereby to enable the video game server to request and obtain, from the body scan server, body scan derived data that is required to enable defining of the relevant personalised character.

In any event, the delivered set of body scan data is processed by the video game server thereby to enable generation of a virtual object based on the body scan data, such as a personalised virtual character, which is configured for rendering at a client device. In this manner, users of body scanning booths are able to conveniently access functionality for personalised gaming experiences.

One embodiment provides a scanning booth including, as discussed herein, a booth body defining an interior containing a space; scanning hardware configured to generate scanning data for a user within the space; and a user interface device. In some embodiments, the user interface is configured to enable a user to select a desired video game from a set of available video games. For example, information relating to video games which provide charactered customisation functionalities is presented via the user interface. In some embodiments this information is pushed by video game servers via an API that enables communication with server 110, and hence delivery of information to distributed scanning booths. This may be directed to owners of games, and/or prospective owners of games (for example video games may be advertised by virtue of their integration with the body scanning framework).

An output of the scanning booth (for example a network connection) is configured to communicate to the body scan management server: (i) data derived from the scanning data; and (ii) data representative of the user's selection of the desired video game (or games). As a result, data derived from the scanning data is made available to a video game server associated with the desired video game, thereby to enable defining of a virtual object based on the data derived from the scanning data.

Figure 4C:
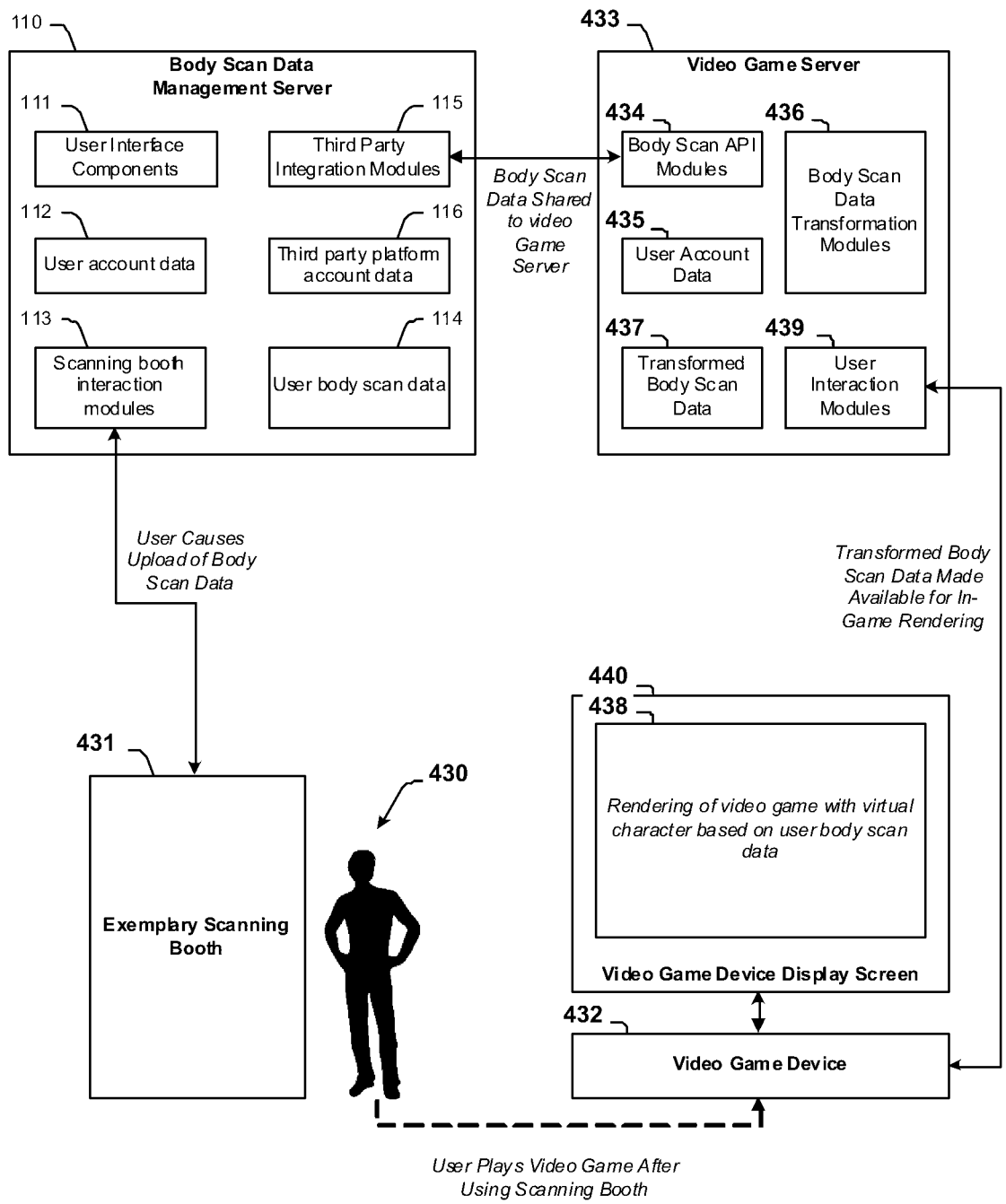
FIG. 4C illustrates a framework for interfacing body scan data with video games.

An exemplary framework is illustrated in FIG. 4C. This includes the same server 110 illustrated in FIG. 1A, for the sake of continuity.

In the example of FIG. 4, a user 430 visits an exemplary scanning booth 431, thereby to undergo a body scan. User 430 subsequently interacts with a video game device 432 (which may be a console, PC, mobile device, and so on), which includes a display screen 440.

Scanning booth 110 is in communication with server 110, which in turn (via third party integration modules 115) interacts with a video game server 433. Video game server 433 includes body scan API modules 434, which enable data exchange between sever 433 and server 110. As discussed above, this data exchange includes user identification, either based on user account data 112 at server 110, or by user account data 435 at server 433 (depending on whether the transfer process is initiated via booth 431 or device 432). Assuming successful user authentication between the servers, user body scan data is shared to server 433. Body scan data transformation modules 436 are configured to process body scan data obtained from server 110, thereby to define transformed body scan data 437. Data 437 enables the defining (and subsequent rending) of virtual objects representative of personalised virtual characters in video game rendering 438. User interaction modules 439 enable interaction between server 433 and a plurality of devices 402.

Figure 2K:
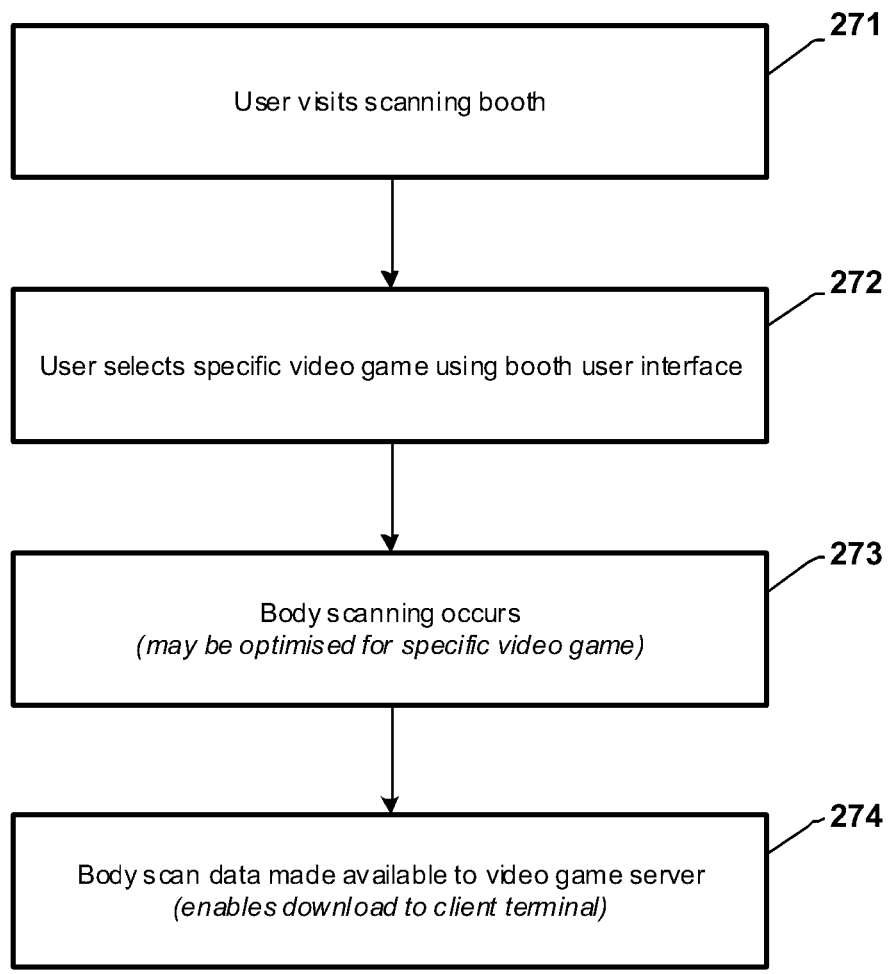
Figure 2L:
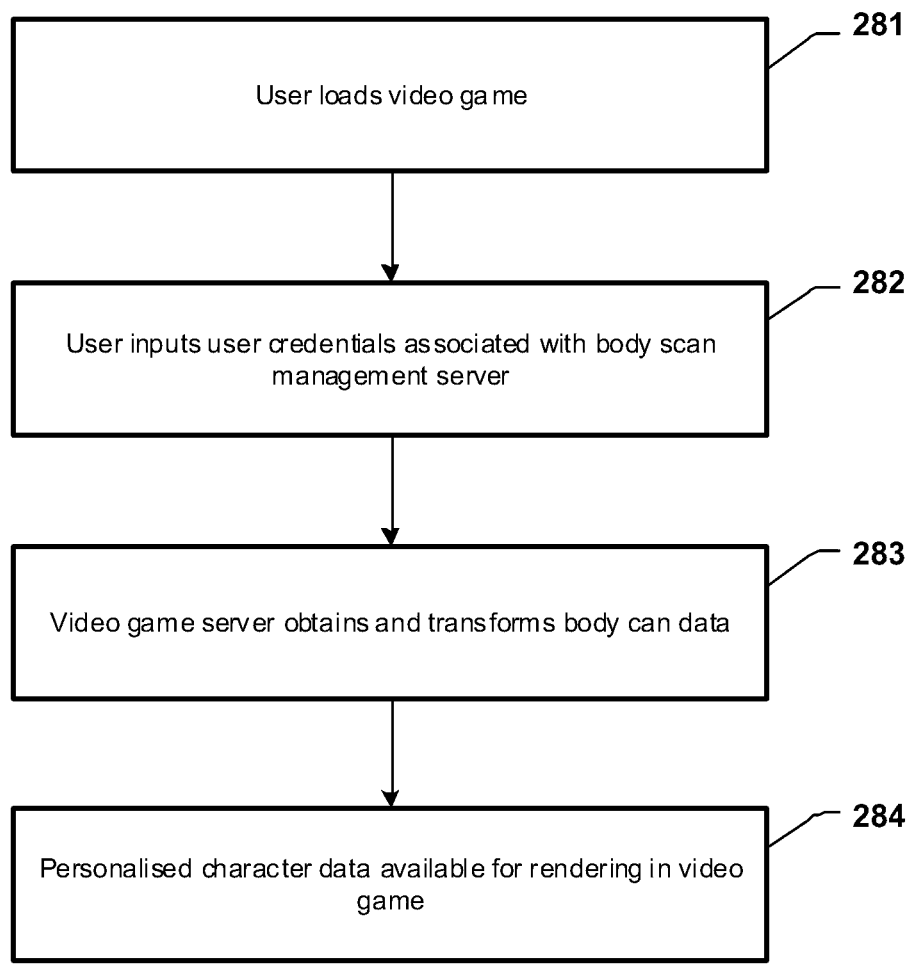

FIG. 2K and FIG. 2L illustrate exemplary process flows according to embodiments. These are provided as examples only.

In the example of FIG. 2K, a user first visits a scanning booth at 271. The user interacts with a user interface device provided by the scanning booth thereby to select a desired video game at 272. Body scanning then occurs at 273, in some cases being body scanning optimised for a specific video game (for example, via the API, a given video game server provides data representative of particular scanning requirements for a given game, which may in some cases include scanning a user who is wearing a specific outfit or the like). The body scan data is then made available to the video game server at 274. This may be via video game server credentials inputted at the scanning booth, or body scan server credentials subsequently inputted via a video game user interface.

In the example of FIG. 2L, the process flow commences with a user loading a video game at 281, and via a video game user interface the user inputs user credentials associated with the body scan management server at 282. This enables a video game server to obtain body scan data, and transform that data, at 283, allowing customised character data to be made available for rendering in the video game at 284.

Body Appearance Forecasting and Progress Tracking Based on Defined Goals and/or Activity Programs The preceding examples relate to tracking of progress in terms of variations in body shape. In some embodiments, functionality is provided thereby to provide forecasting in relation to body shape. On overview, existing physical attribute data (e.g. derived from body scan data) is processed via one or more transformation algorithms thereby to define forecasted future physical attribute data. The algorithms may be associated with defined goals (for example muscle gain or weight loss), or activity programs (which are associated with anticipated outcomes in terms of muscle gain and/or weight loss).

Figure 2M:
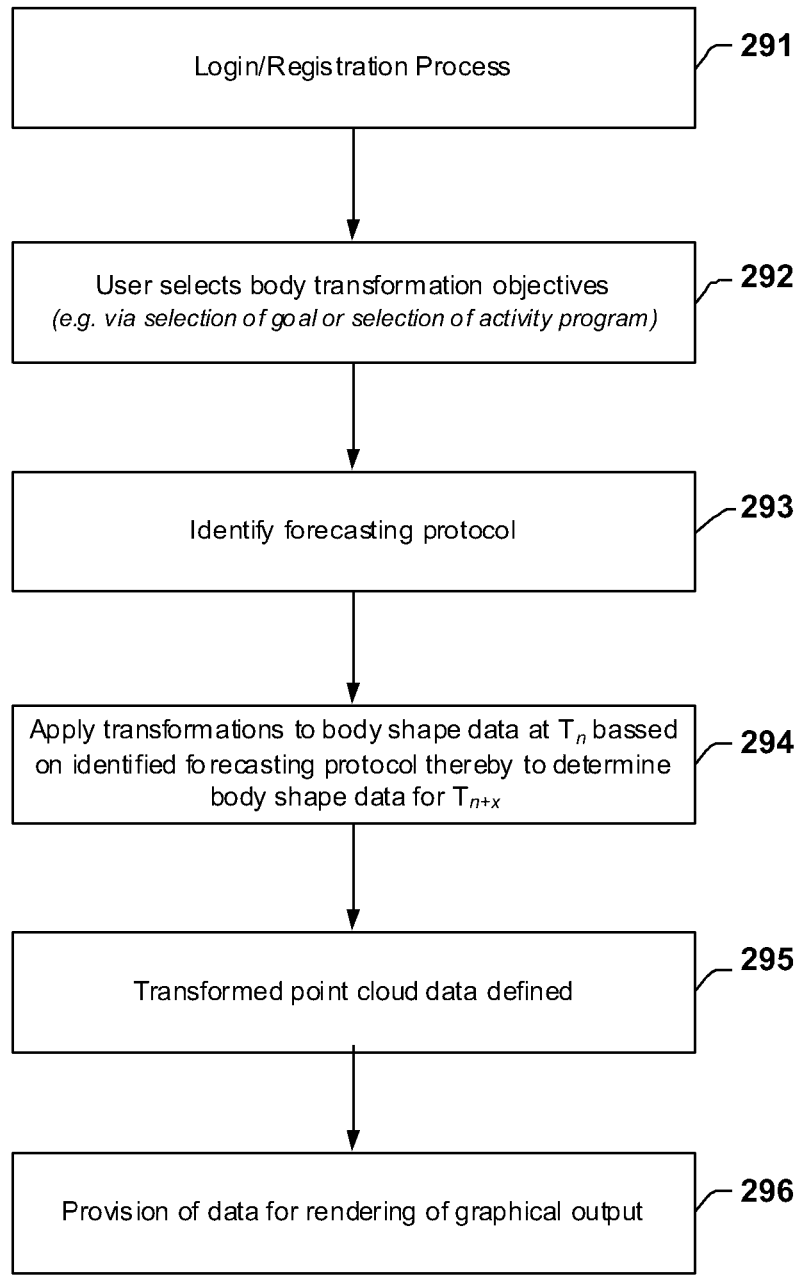

An exemplary method is shown in FIG. 2M. Functional block 291 represents a login/registration process. This includes authenticating a user $U_1$, the user $U_1$ being associated with first user record data, wherein the first user data includes a first set of user physical attribute data associated with a time n ($PAD_1T_n$), wherein the set of physical attribute data is derived from a three-dimensional body scanning process.

Functional block 292 represents a process including the user selecting body transformation objectives. For example, the forecasting is based on either or both of: (i) a defined goal; or (ii) an activity program. In relation to (i), the forecasting is in some embodiments based upon a body transformation goal, for example in relation to weight loss and/or muscle gain. For instance, this may be percentage-based (such as a 5% reduction in body fat) or the like. In practice, a user provides a request/query associated with a defined goal (for example "how might I look if I lose 3 kg", or "how might I look if I put on more muscle"). In relation to (ii), the forecasting is in some embodiments based upon an activity platform, for example a training and/or dietary regime. This is in some cases associated with percentage-based body variations (such as a 5% reduction in body fat, 5% increase in muscles) or the like, which is in some embodiments tailored across specific body regions (for example a given training program might be tailored towards developing certain muscles). In practice, a user selects an activity program, and is shown how they might look over time if they follow that program.

Functional block 293 includes identifying a forecasting protocol based on the user's selection of transformation objectives. The forecasting protocol is in turn associated with transformations that are applied to physical attribute data thereby to define forecasted physical attribute data at a future time. In this regard, functional block 294 represents a process including processing the physical attribute data associated with time n ($PAD_1T_n$) based on the a selected forecasting protocol thereby to define forecasted user physical attribute data for user $U_1$ associated with a time n+x ($PAD_1T_{n+x}$). In this embodiment, the physical attribute data is represented as a point cloud, and transformed point cloud data is defined at 295.

Functional block 296 represents a process including providing output configured to enable rendering, at a client device associated with user $U_1$, a graphical object representative of $PAD_1T_{n+x}$.

In some embodiments the graphical object is representative of the relationship between $PAD_1T_n$ and $PAD_1T_{n+x}$, for example using overlay techniques discussed further above.

In some embodiments a combination of tracking and forecasting is implemented, such that a user is enabled to compare actual body shape transformation progress against both previous body shape and forecasted data. This in some embodiments enables generation of updated forecasts based on observation that a given user is displaying better/worse than expected rates of progress. In some embodiments, comparison between progress and forecasting is used to enable a user to obtain additional instructional information, for example advice from a personal trainer associated with a given selected activity program.

Marketing Based on Size, Including Overstock Marketing

In some embodiments, technologies discussed herein are implemented thereby to enable marketing based on consumer size. A particular example of this is overstock marketing, where a vendor has a surplus of items in a particular size.

One embodiment provides a computer implemented method for configured to provide vendors access to potential customers based on customer size information, the method including: maintaining access to a database including data representative of consumer body dimension attributes, wherein the data is derived from 3-dimensional body scans; receiving a request from a vendor, wherein the request is indicative of desired consumer body attributes, wherein the desired body attributes correspond to appropriate sizes for a set of one or more products to be marketed; identifying, in the database including data representative of consumer body dimension attributes, a set of one or more consumers satisfying the desired body attributes; and providing data representative of the set of one or more consumers.

In some embodiments, the method includes providing data representative of the set of one or more consumers to the vendor, which may allow the vendor to provide specific marketing materials.

In some embodiments the method includes providing data representative of the set of one or more consumers includes providing data thereby to enable filtering of web page information rendered at a client terminal associated with a given consumer, such that the given consumer is enabled only to view predetermined data relating to the set of one or more products to be marketed in the case that the given consumer belongs to the set of one or more consumers. For example, a consumer performs a body-scan server associated authentication process at a vendor website. In the case that the vendor has subscribed to a marketing plan which includes identification of users having body attributes corresponding to that consumer, the website automatically configures to make visible to the consumer specific size-appropriate goods. This is useful in clearing overstock clothing in specific sizes; a vendor may subscribe to users having body sized appropriate to that clothing, thereby to streamline the process of marketing (and ideally selling) the relevant garments.

Another embodiment provides a computer implemented method for configured to provide vendors access to potential customers based on customer size information, the method including: Identifying a set of products to be marketed via on online marketplace, wherein the set of products as associated with common sizing parameters; determining a set of body attributes associated with the common sizing parameters; Identifying, in a database including data representative of consumer body dimension attributes, wherein the data is derived from 3-dimensional body scans, set of one or more consumers having the determined body attributes; and providing data thereby to enable display of the set of products, via the online marketplace to only the set of one or more consumers. Again, this may be subscription based, such that a marketing premium paid by a vendor is related to one or more of (i) a range of body sizes; (ii) a number of consumers falling into a desired body size range; and (iii) a number of ranges of body sizes.

In some embodiments, frameworks described herein are configured to enable lead-generation (for example in a marketing context) based on forecasted changes in body characteristics. As general context, within the example of clothing, as a given person changes in size they are likely to require new clothing. Furthermore, in the case that a person moves down in clothing sizes (for example as result of an exercise/dietary regime), that person can be reasonably expected to have an increased desire to purchase new clothing. Embodiments of technology described herein identify these factors, and provide opportunities for directed marketing accordingly. For example, businesses are enabled to market to potential customers' based upon a forecast of users' changing body shapes and/or behaviours.

Some embodiments provide this functionality by executing a size change event identification process. This is a process that is configured to identify one or more size change events, wherein each size change event is associated with a respective consumer for whom the database includes data representative of consumer body dimension attributes derived from 3-dimensional body scan. In preferred embodiments, the size change event identification process is configured to identify a size change event for a given consumer, user $U_1$, in the case that the user is forecasted to move a first garment size to a second garment size.

In some embodiments the forecasting is based on identification that the consumer has registered to participate in a particular activity program (for example a diet and/or exercise program). Each diet and/or exercise program is associated with a forecasted timeline for a body transformation, which may be variable based on attributes of a user (for example the user's initial weight, BMI, localised fat stores, and so on).

In some embodiments the forecasting is based on identification of a body transformation trend identified based on comparison of the relationship between body scan derived data at different times $(PAD_1T_n)$ and $(PAD_1T_{n+x})$. This may identify a trend for future forecasting, or in some cases be used as a trigger to market new goods and/or services based on the consumer's new size.

One exemplary size change event identification process is configured to identify a size change event for a given consumer, user $U_1$, in the case that:
- user $U_1$ is associated a first set of user physical attribute data associated with a time n $(PAD_1T_n)$;
- user $U_1$ is subsequently associated a second set of user physical attribute data associated with a time n+x $(PAD_1T_{n+x})$; and
- the relationship between $(PAD_1T_n)$ and $(PAD_1T_{n+x})$ indicates that user $U_1$ has moved from a first garment size to a second garment size.

This in some cases enables, for user $U_1$, providing output representative the change events enables marketing of one or more garments at the second garment size. In some cases the output enables marketing of one or more garments at the third garment size based on a size-decreasing trend identified for user $U_1$.

One exemplary size change event identification process is configured to identify a size change event for a given consumer, user $U_1$, in the case that:
- user $U_1$ is associated with first user record data including a first set of user physical attribute data associated with a time n $(PAD_1T_n)$;
- based on execution of a forecasting protocol, $U_1$ is forecasted to be associated with a second set of user physical attribute data associated with a time n+x $(PAD_1T_{n+x})$; and
- the relationship between $(PAD_1T_n)$ and $(PAD_1T_{n+x})$ indicates that user $U_1$ will have moved from a first garment size to a second garment size.

Some embodiments are configured such that subscription requests are received from vendors for the purposes of requesting particular marketing intelligence. That is, a given subscription request is indicative of a set of desired size change events. In the case that the subscription request is granted, providing to the vendor data indicative of identified size change events belonging to the set of desired size change events.

In some embodiments subscription requests include one or more of the following:
- A request for male consumers identified (or forecasted) as moving from Size A to Size B.
- A request for male consumers identified as (or forecasted) moving from Size A to Size B as a result of increased muscle gains.
- A request for male consumers identified (or forecasted) as moving from Size A to Size B as a result of increased muscle gains who are known to be engaging in a training program.
- A request for male consumers identified (or forecasted) as moving from Size A to Size B as a result of increased muscle gains who are known to be engaging in a particular training program.
- A request for female consumers identified as Size A within a predetermined date range, and forecasted to reach Size D within a predetermined date range due to a diet/exercise program.
- A request for consumers of any sex forecasted to change by 2 or more clothing sizes within two months (which is, for example, used to market holiday destinations to tropical destinations).

It will be appreciated that these are examples only. In practice, a vendor is preferably enabled to define a request based on requirements constructed based on marketing desires.

In some embodiments the data indicative of identified size change events belonging to the set of desired size change events enables the vendor to provide marketing information to the desired consumers. In other embodiments the vendor provides the marketing information, and this is delivered via server 110 or an associated server.

In some embodiments a method includes receiving a subscription request from a vendor, wherein the subscription request is indicative of (i) a specific category of size change events; and (ii) marketing data; and in the case that the subscription request is granted, providing the marketing data to one or more consumers in respect of whom a size change event belonging to the specific category of size change events is identified. In other embodiments a method includes receiving a subscription request from a vendor, wherein the subscription request is indicative of (i) a specific category of size change events; and (ii) marketing data delivery rules; and in the case that the subscription request is granted, providing the marketing data to one or more consumers in respect of whom a size change event belonging to the specific category of size change events is identified based on the marketing data delivery rules.

Customisable Mechanical Equipment

In some embodiments, a body scan data management framework as described herein is applied in the context of enabling customisation of mechanical equipment, being mechanical equipment for which one or more movable components are variably positioned based on a user's size. Examples include:

Seats, for example in cars, aeroplanes, and the like.

Overall control environments. For example, this may include, in the context of a vehicle, a seat combines with steering controls, mirrors, and so on.

Medical equipment, which is sized specifically for a given user (such as a patient).

Devices that interact with human body regions, such as massage chairs and the like.

Safety equipment, such as harnesses and braces (for example at amusement parks).

It will be appreciated that there are a multitude of other examples of mechanical equipment to which technology described below may be applied.

In overview, the approach implemented in various embodiments is to define a size-based customisation protocol for a given piece of mechanical equipment, for example a car's driver environment (comprising a seat, starting wheel, and mirrors). The size-based customisation protocol defines positions for each adjustable component based on body size data values (for example lower leg length, upper leg length, torso length, neck length, arm length, and so on). This provides a far greater scope for personalised control than a rough parameter such as user height. Furthermore, it will be appreciated that such body size data values are readily extracted from a body scanning process as described herein.

One embodiment provides a computer implemented method for managing body scan data, the method including: receiving data representative of a selection of a customizable mechanical device; identifying a size-based customisation protocol associated with the selected customizable mechanical device; identifying a target user; accessing body size data for the identified target user, wherein the body size data is obtained from a server that maintains access to body attribute data for a plurality of users, wherein the body attribute data is derived from 3D body scanning of each of the plurality of users; applying the identified size-based customisation protocol to the accessed body size data, thereby to define equipment customisation data; and providing output data representative of the equipment customisation data.

The step of receiving data representative of a selection of a customizable mechanical device occurs, in some embodiments, in response to a user selection at a client device. For example, the client device may be a web-browser device (such as a smartphone or PC). In some cases the client device is a scanning booth (for instance a user designates a piece of mechanical equipment prior to scanning, which in some cases may trigger certain scanning optimisation methods). The selection of a customizable mechanical device is in some embodiments defined by reference to a manufacturer, model, or the like. The term "specific" is not intended to indicate a unique device (for example a specific physical example of a specific device). However, in some cases a user identifies not only the specific type of device but also the specific physical instance of the device (e.g. the user's own device).

The size-based customisation protocol associated with the selected customizable mechanical device is identified from one or more databases of customisation protocols. In practice, customisation protocols may be defined by (or in collaboration with) device manufacturers (who, for example, pay a license fee to a body scan management service provider). Alternately, a body scan management service provider (or other third party) in some cases defines protocols without involvement of a device manufacturer. In some embodiments each size-based customisation protocol includes an algorithm (or other process) that causes defining of a data set in response to processing of size value data derived from body scan data.

Identifying a target user is preferably achieved by input of user credentials known to a body scan data management server, thereby to uniquely identify a known user (and hence identify that user's body scan data).

In some embodiments applying the size-based customisation protocol includes executing one or more processes that receive as input body dimension values provided by the accessed body size data.

The step of providing output data representative of the equipment customisation data occurs in various ways, depending on embodiment design, and depending on characteristics of the relevant equipment. In relation to the latter, the following examples are noted:

Some equipment is configured to communicate via Internet (in some cases through a network enabled control unit). In some such cases, the data representative of the equipment customisation data may be communicated from a server device to the mechanical equipment (or control unit). In some embodiments providing output data representative of the equipment customisation data includes making configuration data available via a server accessible by a physical instance of the customizable mechanical device, and subsequently apply that equipment customisation data. In some such cases an operator inputs user credential data into the equipment, thereby to enable identification of correct configuration data at the server.

Some equipment is configured to communicate with a local device, such as a smartphone (e.g. via Bluetooth). In some such cases, the data representative of the equipment customisation data may be downloaded to an appropriate local device (via the Internet), and then provided to the equipment. One embodiment provides a computer implemented method wherein providing output data representative of the equipment customisation data includes providing a data set that is downloadable to a device, wherein a physical instance of the customizable mechanical device is configured to read the data set and apply the equipment customisation data.

Some equipment is configured to read a portable memory device, such as a flash memory device (e.g. a SD/FC card, USB drive, or the like). In some such cases, the data representative of the equipment customisation data may be written to an appropriate memory device (via an Internet enabled writing device), and then provided to the equipment.

Some equipment includes an input device, for example an input device configured to receive an alphanumeric code (for example the code is able to be translated thereby to determine position settings). In some such cases, the data representative of the equipment customisation data is embedded in an alphanumeric code, and that code provided to a user (such that the user can subsequently input the code into the equipment). One embodiment provides a computer implemented method wherein providing output data representative of the equipment customisation data includes providing a code, wherein a physical instance of the customizable mechanical device is configured to receive the code, and translate that code thereby to apply the equipment customisation data.

These are a selection of examples only.

In some embodiments the equipment customisation data is configured to be applied by a physical instance of the selected customizable mechanical device thereby to cause the physical instance of the customizable mechanical device to self-configure in a manner tailored to the target user.

Figure 2N:
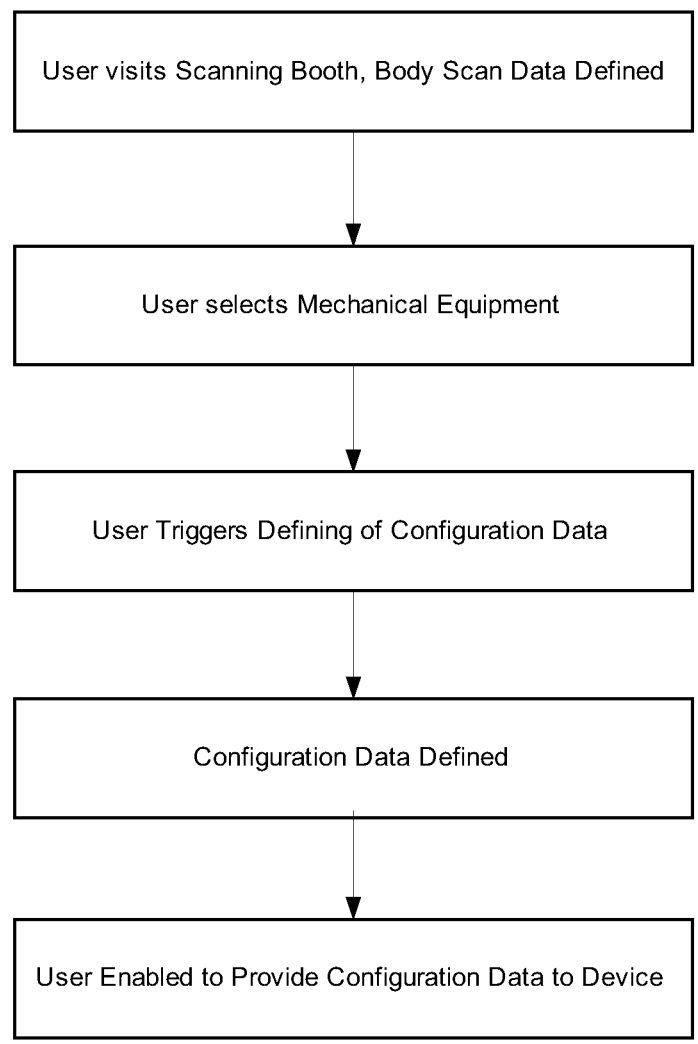

FIG. 2N illustrates an exemplary process flow according to one embodiment. In this example, a user first visits a scanning booth (which may be an in-home scanning hardware arrangement), and body scan data is defined. Subsequently, either via the booth or via another device (in some cases being the equipment itself, or a device in direct communication with the equipment), a user causes a selection of a mechanical device, and triggers defining of configuration data for that device. The configuration data is defined, and the user enabled to provide it to the device. In one alternate process flow the user selects the mechanical equipment prior to scanning, thereby to enable optimised scanning for the relevant equipment.

FIG. 5A to FIG. 5D illustrate exemplary frameworks for enabling configuration of configurable equipment 521 via a control/input device 520, using body scan data made available by server 110 of FIG. 1A.

In these examples, a scanning booth 500 is in communication with server 110, which in turn (via third party integration modules 115) interacts with a mechanical equipment configuration server 510. Server 510 includes body scan API modules 511, which enable data exchange between sever 510 and server 110. For example, this data exchange includes user identification, either based on user account data 112 at server 100, or by user account data 512 at server 510 (depending on whether the transfer process is initiated via booth 500 or, for example, a device 520). Assuming successful user authentication between the servers, user body scan data is shared to server 510. Device configuration rules 513 are configured to process body scan data obtained from server 110, thereby to define device configuration data 514. Data 514 is made available for download via user interaction modules 515.

Figure 5A:
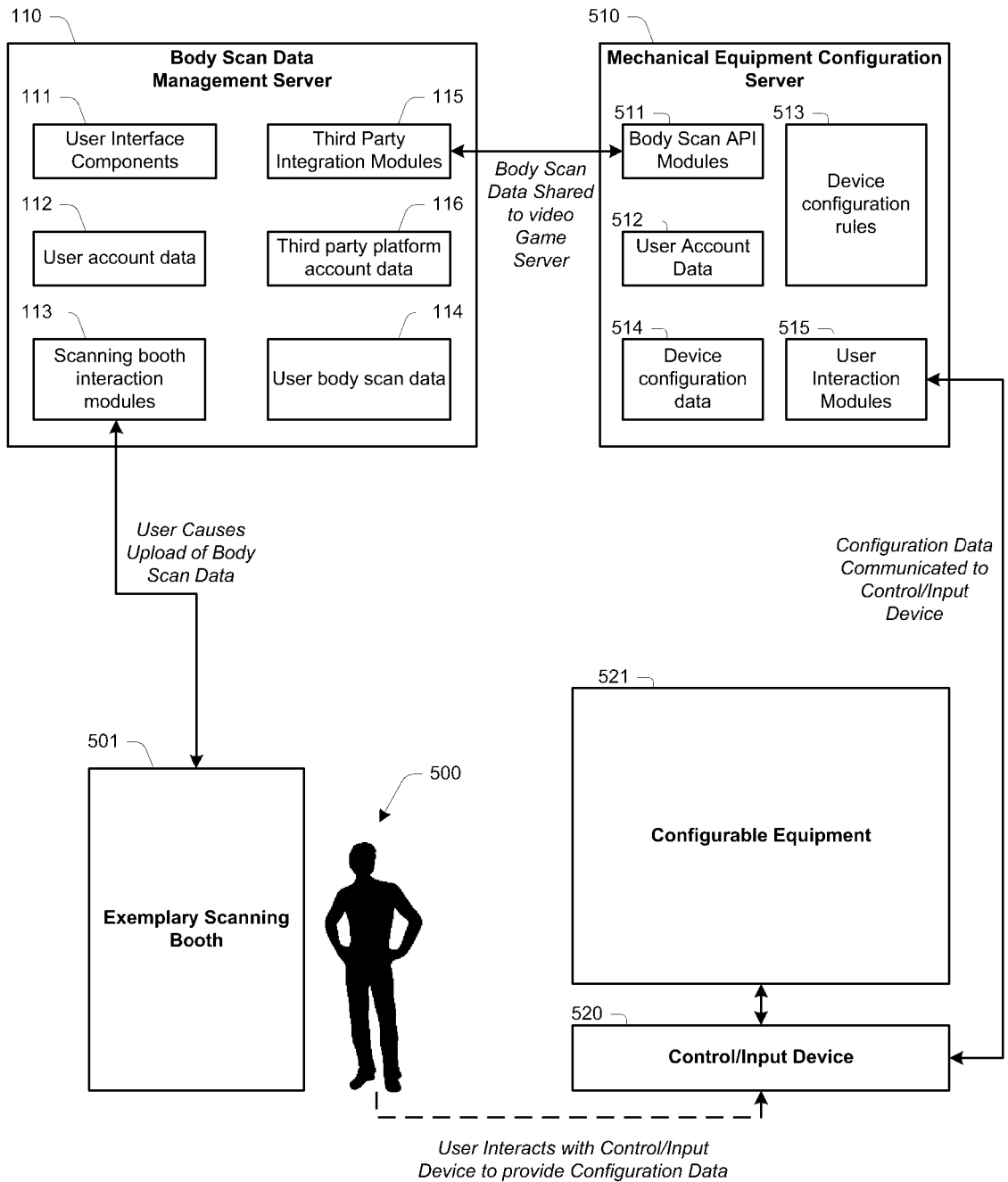
FIG. 5A to FIG. 5D illustrate exemplary frameworks for interfacing body scan data with configurable equipment.
Figure 5B:
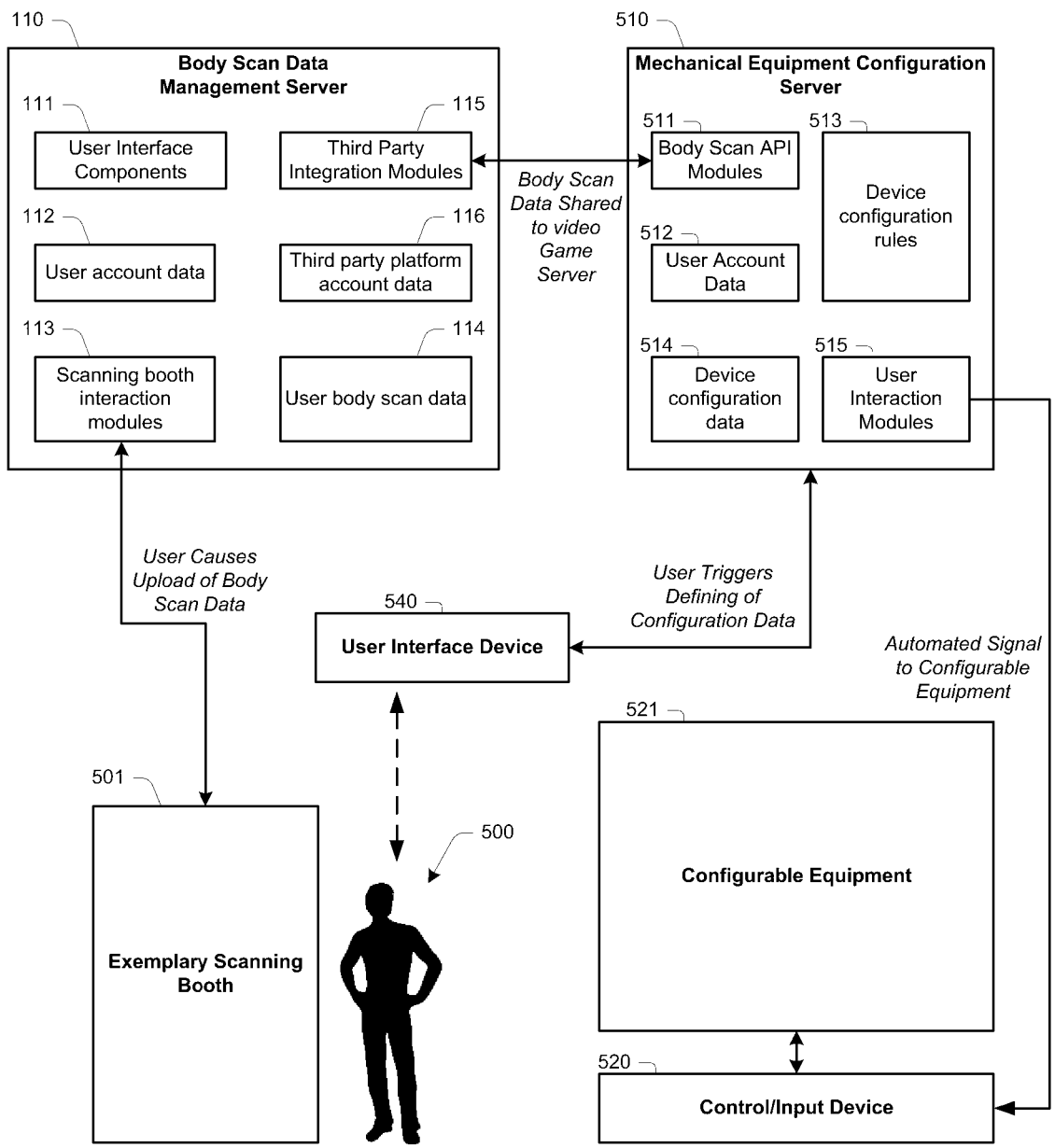
Figure 5C:
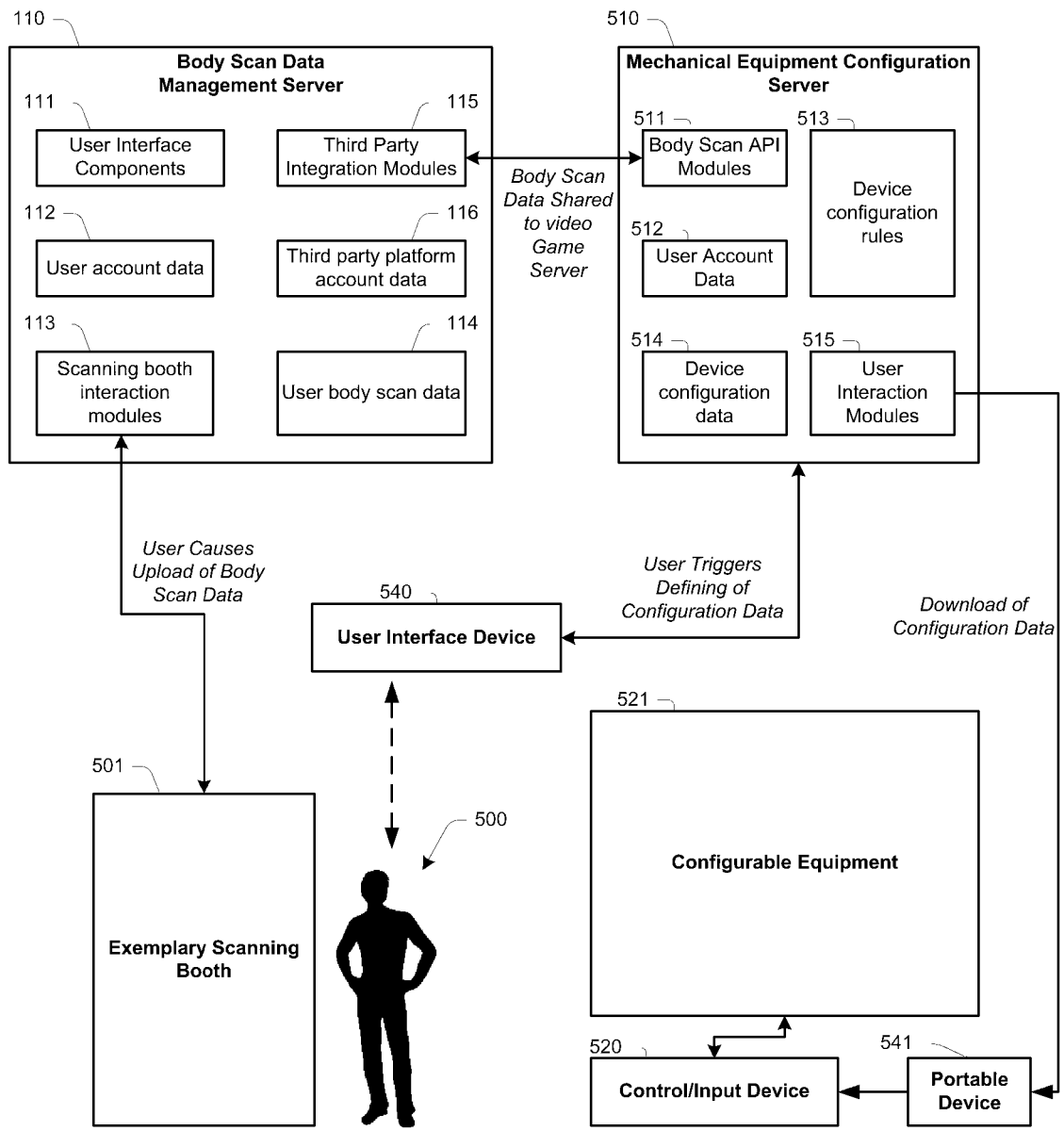
Figure 5D:
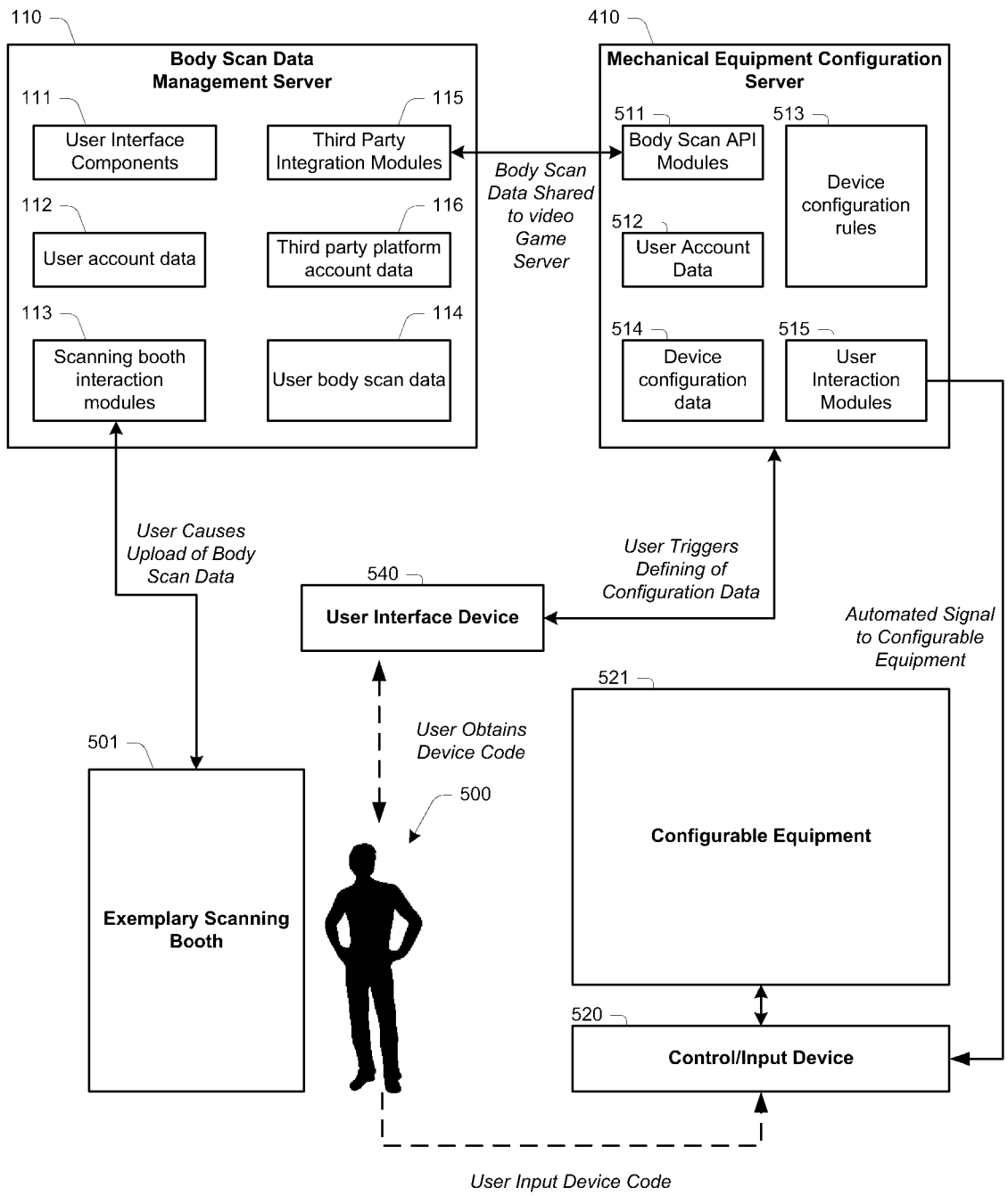

In the example of FIG. 5A, control device 520 communicates over the Internet with server 510. In the example of FIG. 5B, user 500 interacts with server 510 via a user interface device 540 to trigger defining of configuration data, and cause an automated download of that data to device 520. In the example of FIG. 5C, such download is to a portable device 541 (which may be the same hardware as device 540), and device 541 provides the configuration data to device 520. Portable device 541 may be a passive memory device. In the example of FIG. 5D, user 500 interacts with server 510 via a user interface device 540 to trigger defining of configuration data, which takes the form of a code, which user 500 subsequently inputs into device 520.

Exemplary Client Server Framework

Figure 3:
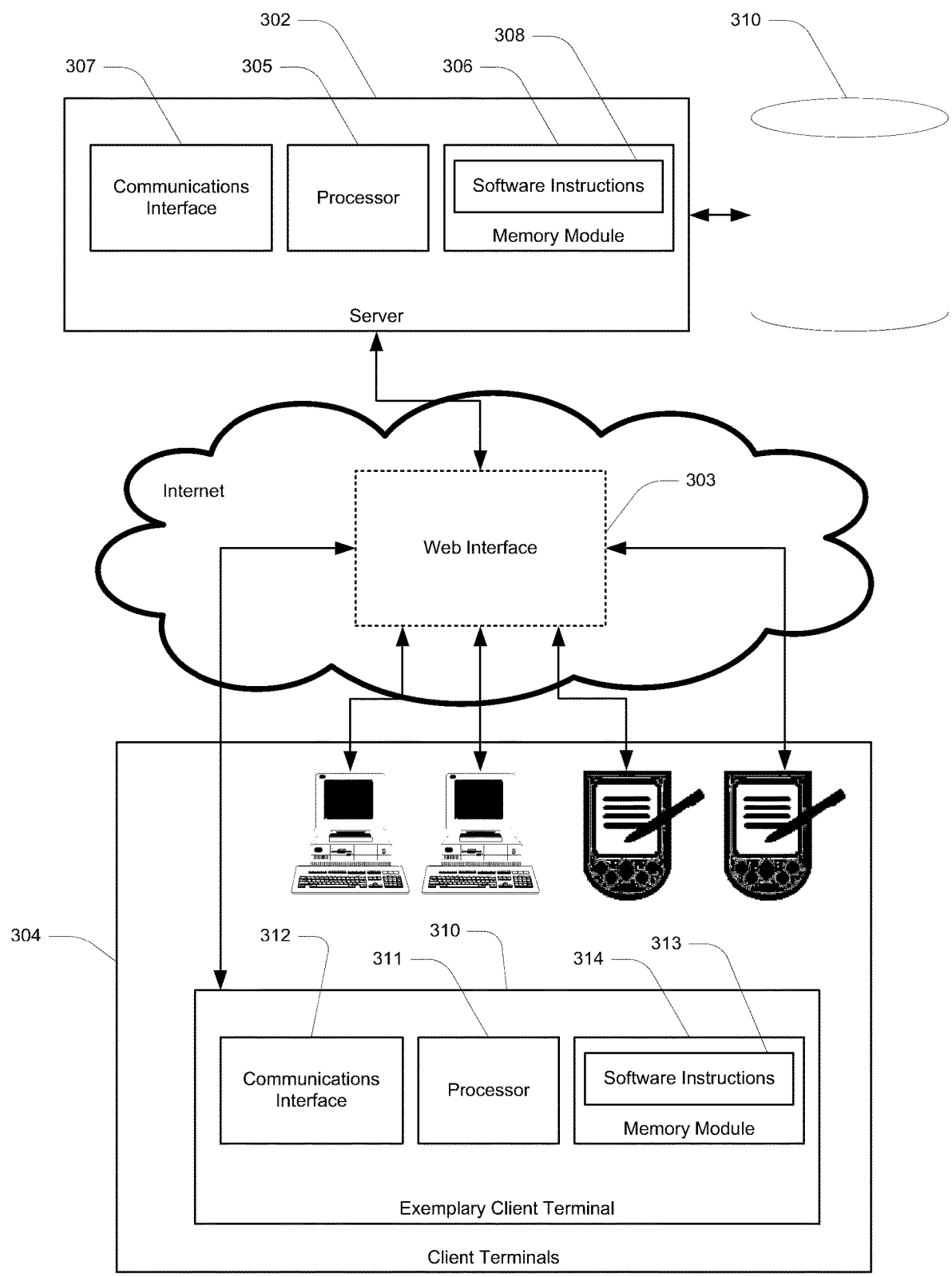
FIG. 3 illustrates a client-server framework leveraged by various embodiments.

In some embodiments, methods and functionalities considered herein leverage a client-server framework, for example as illustrated in FIG. 3.

In some embodiments, methods and functionalities considered herein are implemented by way of a server, as illustrated in FIG. 3. In overview, a web server 302 provides a web interface 303. This web interface is accessed by the parties by way of client terminals 304. In overview, users access interface 303 over the Internet by way of client terminals 304, which in various embodiments include the likes of personal computers, PDAs, cellular telephones, gaming consoles, and other Internet enabled devices.

Server 302 includes a processor 305 coupled to a memory module 306 and a communications interface 307, such as an Internet connection, modem, Ethernet port, wireless network card, serial port, or the like. In other embodiments distributed resources are used. For example, in one embodiment server 302 includes a plurality of distributed servers having respective storage, processing and communications resources. Memory module 306 includes software instructions 308, which are executable on processor 305.

Server 302 is coupled to a database. In further embodiments the database leverages memory module 306.

In some embodiments web interface 303 includes a website. The term "website" should be read broadly to cover substantially any source of information accessible over the Internet or another communications network (such as WAN, LAN or WLAN) via a browser application running on a client terminal. In some embodiments, a website is a source of information made available by a server and accessible over the Internet by a web-browser application running on a client terminal. The web-browser application downloads code, such as HTML code, from the server. This code is executable through the web-browser on the client terminal for providing a graphical and often interactive representation of the website on the client terminal. By way of the web-browser application, a user of the client terminal is able to navigate between and throughout various web pages provided by the website, and access various functionalities that are provided.

Although some embodiments make use of a website/browser-based implementation, in other embodiments proprietary software methods are implemented as an alternative. For example, in such embodiments client terminals 304 maintain software instructions for a computer program product that essentially provides access to a portal via which a framework is accessed (for instance via an iPhone app or the like).

In general terms, each terminal 304 includes a processor 311 coupled to a memory module 314 and a communications interface 312, such as an internet connection, modem, Ethernet port, serial port, or the like. Memory module 314 includes software instructions 313, which are executable on processor 311. These software instructions allow terminal 304 to execute a software application, such as a proprietary application or web browser application and thereby render on-screen a user interface and allow communication with server 302. This user interface allows for the creation, viewing and administration of profiles, access to the internal communications interface, and various other functionalities.

CONCLUSIONS AND INTERPRETATION

It will be appreciated that the disclosure above provides various significant devices, frameworks and methodologies for enabling user-driven determination of body size and shape information and utilisation of such information across a networked environment.

Unless specifically stated otherwise, as apparent from the following discussions, it is appreciated that throughout the specification discussions utilizing terms such as "processing," "computing," "calculating," "determining", analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. Each processor may include one or more of a CPU, a graphics processing unit, and a programmable DSP unit. The processing system further may include a memory subsystem including main RAM and/or a static RAM, and/or ROM. A bus subsystem may be included for communicating between the components. The processing system further may be a distributed processing system with processors coupled by a network. If the processing system requires a display, such a display may be included, e.g., a liquid crystal display (LCD) or a cathode ray tube (CRT) display. If manual data entry is required, the processing system also includes an input device such as one or more of an alphanumeric input unit such as a keyboard, a pointing control device such as a mouse, and so forth. The term memory unit as used herein, if clear from the context and unless explicitly stated otherwise, also encompasses a storage system such as a disk drive unit. The processing system in some configurations may include a sound output device, and a network interface device. The memory subsystem thus includes a computer-readable carrier medium that carries computer-readable code (e.g., software) including a set of instructions to cause performing, when executed by one or more processors, one of more of the methods described herein. Note that when the method includes several elements, e.g., several steps, no ordering of such elements is implied, unless specifically stated. The software may reside in the hard disk, or may also reside, completely or at least partially, within the RAM and/or within the processor during execution thereof by the computer system. Thus, the memory and the processor also constitute computer-readable carrier medium carrying computer-readable code.

Furthermore, a computer-readable carrier medium may form, or be included in a computer program product.

In alternative embodiments, the one or more processors operate as a standalone device or may be connected, e.g., networked to other processor(s), in a networked deployment, the one or more processors may operate in the capacity of a server or a user machine in server-user network environment, or as a peer machine in a peer-to-peer or distributed network environment. The one or more processors may form a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine.

Note that while diagrams only show a single processor and a single memory that carries the computer-readable code, those in the art will understand that many of the components described above are included, but not explicitly shown or described in order not to obscure the inventive aspect. For example, while only a single machine is illustrated, the term "machine" shall also be taken to include any collection of machines that individually or jointly execute a set (or multiple sets) of instructions to perform any one or more of the methodologies discussed herein.

Thus, one embodiment of each of the methods described herein is in the form of a computer-readable carrier medium carrying a set of instructions, e.g., a computer program that is for execution on one or more processors, e.g., one or more processors that are part of web server arrangement. Thus, as will be appreciated by those skilled in the art, embodiments of the present invention may be embodied as a method, an apparatus such as a special purpose apparatus, an apparatus such as a data processing system, or a computer-readable carrier medium, e.g., a computer program product. The computer-readable carrier medium carries computer readable code including a set of instructions that when executed on one or more processors cause the processor or processors to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code embodied in the medium.

The software may further be transmitted or received over a network via a network interface device. While the carrier medium is shown in an exemplary embodiment to be a single medium, the term "carrier medium" should be taken to include a single medium or multiple media (e.g., a centralized or distributed database, and/or associated caches and servers) that store the one or more sets of instructions. The term "carrier medium" shall also be taken to include any medium that is capable of storing, encoding or carrying a set of instructions for execution by one or more of the processors and that cause the one or more processors to perform any one or more of the methodologies of the present invention. A carrier medium may take many forms, including but not limited to, non-volatile media, volatile media, and transmission media. Non-volatile media includes, for example, optical, magnetic disks, and magneto-optical disks. Volatile media includes dynamic memory, such as main memory. Transmission media includes coaxial cables, copper wire and fiber optics, including the wires that comprise a bus subsystem. Transmission media also may also take the form of acoustic or light waves, such as those generated during radio wave and infrared data communications. For example, the term "carrier medium" shall accordingly be taken to included, but not be limited to, solid-state memories, a computer product embodied in optical and magnetic media; a medium bearing a propagated signal detectable by at least one processor of one or more processors and representing a set of instructions that, when executed, implement a method; and a transmission medium in a network bearing a propagated signal detectable by at least one processor of the one or more processors and representing the set of instructions.

It will be understood that the steps of methods discussed are performed in one embodiment by an appropriate processor (or processors) of a processing (i.e., computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

It should be appreciated that in the above description of exemplary embodiments of the invention, various features of the invention are sometimes grouped together in a single embodiment, FIG., or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A computer implemented method for enabling tracking of body shape variations, the method comprising:
   receiving a subscription request from a vendor, wherein the subscription request is indicative of a specific category of size change events and is defined by the vendor based on marketing desires;
   authenticating a user $U_1$, the user $U_1$ being associated with first user record data, wherein the first user record data includes a first set of user physical attribute data associated with a time n ($PAD_1T_n$), wherein the first set of user physical attribute data is derived from a three-dimensional body scanning process;
   receiving input representative of a further set of user physical attribute data, the further set being associated with a time n+x ($PAD_1T_{n+x}$);
   performing an analysis of a relationship between $PAD_1T_n$ and $PAD_1T_{n+x}$;
   identifying a size change event in a case that the relationship between $PAD_1T_n$ and $PAD_1T_{n+x}$ indicates that the user Ui has moved from a first garment size to a second garment size; and
   in response to identifying that the size change event of the user $U_1$ belongs to the specific category of size change events defined in the subscription request from the vendor:
      providing data indicative of the size change event to the vendor and allowing the vendor to provide marketing information to the user $U_1$.

2. The method according to claim 1 wherein each set of three dimensional body scan data includes a three dimensional point cloud, and wherein analysis of relationships between $PAD_1T_n$, and $PAD_1T_{n+x}$ is based on comparison of the respective point clouds.

3. The method according to claim 2 wherein comparison of the point clouds includes utilisation of vector mathematics to determine spatial variations between corresponding points.

4. The method according to claim 2 further comprising providing output configured to enable rendering, at a client device associated with the user $U_1$, a graphical object representative of the relationship between $PAD_1T_n$, and $PAD_1T_{n+x}$, wherein the graphical object is defined based on an overlay of the point cloud for $PAD_1T_{n+x}$, with respect to the point cloud at $PAD_1T_n$.

5. The method according to claim 4 wherein the graphical object provides visual indicators representative of variations between $PAD_1T_n$, and $PAD_1T_{n+x}$.

6. The method according to claim 5 wherein the visual indicators include colours.

7. The method according to claim 5 wherein a first visual indicator is used to identify an increase in localised body size, and a second visual indicator is used to identify a decrease in localised body size.

8. The method according to claim 5 wherein a first visual indicator is used to identify an identified improvement towards a predefined body goal, and a second visual indicator is used to identify regression away from the predefined body goal.

9. The method according to claim 5 wherein the graphical object includes a stylised body shape generated based on the point cloud data.

10. The method according to claim 4 wherein the client device associated with the user is a mobile device.

11. The method according to claim 4 wherein the client device associated with the user is a scanning booth at which the user is located.

12. A non-transitory computer readable storage medium carrying computer-readable code including a set of instructions to perform, when executed by one or more processors, a method according to claim 1.

13. A computer implemented method for providing graphical data representative of forecasted body shape variations, the method comprising:

receiving a subscription request from a vendor, wherein the subscription request is indicative of a specific category of size change events and is defined by the vendor based on marketing desires;

authenticating a user $U_1$, the user $U_1$ being associated with first user record data, wherein the first user record data includes a first set of user physical attribute data associated with a time n ($PAD_1T_n$), wherein the set of user physical attribute data is derived from a three-dimensional body scanning process;

processing the user physical attribute data associated with time n ($PAD_1T_n$) based on a selected forecasting protocol thereby to define forecasted user physical attribute data for the user $U_1$ associated with a time n+x ($PAD_1T_{n+x}$);

identifying a size change event in a case that the relationship between $PAD_1T_n$ and $PAD_1T_{n+x}$ indicates that the user $U_1$ is forecasted to move from a first garment size to a second garment size; and in response to identifying that the size change event of the user $U_1$ belongs to the specific category of size change events defined in the subscription request from the vendor:

providing data indicative of the size change event to the vendor and allowing the vendor to provide marketing information to the user $U_1$.

14. The method according to claim 13 including providing output configured to enable rendering, at a client device associated with the user $U_1$, a graphical object representative of the relationship between $PAD_1T_n$, and $PAD_1T_{n+x}$.

15. The method according to claim 14 wherein each set of three dimensional body scan data includes a three dimensional point cloud, and wherein analysis of relationships between $PAD_1T_n$, and $PAD_1T_{n+x}$ is based on comparison of the respective point clouds, wherein comparison of the point clouds includes utilisation of vector mathematics to determine spatial variations between corresponding points and wherein the graphical object is defined based on an overlay of the point cloud for $PAD_1T_{n+x}$, with respect to the point cloud at $PAD_1T_n$.

16. The method according to claim 15 wherein the graphical object provides visual indicators representative of variations between $PAD_1T_n$, and $PAD_1T_{n+x}$ and wherein the visual indicators include colours and the graphical object includes a stylised body shape generated based on the point cloud data.

17. The method according to claim 16 wherein a first visual indicator is used to identify an increase in localised body size, and a second visual indicator is used to identify a decrease in localised body size.

18. The method according to claim 16 wherein a first visual indicator is used to identify an identified improvement towards a predefined body goal, and a second visual indicator is used to identify regression away from the predefined body goal.

19. The method according to claim 13 wherein the selected forecasting protocol is selected from a set of available forecasting protocols.

20. The method according to claim 19 wherein each forecasting protocol is associated with either or both of: (i) a defined goal; or (ii) an activity program.

* * * * *